US009131868B2

(12) United States Patent
Kozuka et al.

(10) Patent No.: US 9,131,868 B2
(45) Date of Patent: Sep. 15, 2015

(54) HEARING DETERMINATION SYSTEM, AND METHOD AND PROGRAM FOR THE SAME

(75) Inventors: Kazuki Kozuka, Osaka (JP); Shinobu Adachi, Nara (JP); Koji Morikawa, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 572 days.

(21) Appl. No.: 13/564,390

(22) Filed: Aug. 1, 2012

(65) Prior Publication Data

US 2012/0294451 A1   Nov. 22, 2012

Related U.S. Application Data

(63) Continuation of application No. PCT/JP2011/003237, filed on Jun. 8, 2011.

(30) Foreign Application Priority Data

Jun. 11, 2010   (JP) ................................. 2010-134240

(51) Int. Cl.
*A61B 5/04*   (2006.01)
*H04R 29/00*   (2006.01)
*A61B 5/0484*   (2006.01)
*H04R 25/00*   (2006.01)

(52) U.S. Cl.
CPC ............ *A61B 5/04845* (2013.01); *H04R 25/70* (2013.01)

(58) Field of Classification Search
None
See application file for complete search history.

(56) References Cited

U.S. PATENT DOCUMENTS

| 5,282,475 A * | 2/1994 | Urbach et al. ................ 600/544 |
| 5,755,230 A | 5/1998 | Schmidt et al. |
| 6,602,202 B2 | 8/2003 | John et al. |

(Continued)

FOREIGN PATENT DOCUMENTS

| CN | 101365384 A | 2/2009 |
| CN | 101557753 A | 10/2009 |

(Continued)

OTHER PUBLICATIONS

Office Action for related U.S. Appl. No. 13/561,336, dated Sep. 9, 2014.

(Continued)

*Primary Examiner* — Etsub Berhanu
(74) *Attorney, Agent, or Firm* — Renner, Otto, Boisselle & Sklar, LLP

(57) ABSTRACT

The determination system includes a presented-speech sound control section for determining a speech sound to be presented to a user; auditory/visual stimulation presentation sections for presenting the determined speech sound as an audio/a character; a group-wise summation section for taking a summation of an event-related potential of an electroencephalogram signal of the user for each group of speech sounds; a first determination section for, from the event-related potential having been subjected to summation for each group, making a group-by-group determination of comfortableness as to whether the user is comfortably hearing to the speech sound, to at least determine whether the user is listening to the speech sound with strife, or to determine whether the user is annoyed by the speech sound; and a second determination section for, from the event-related potential, making a speech sound-by-speech sound determination of intelligibility as to whether the user is clearly hearing the speech sound.

19 Claims, 28 Drawing Sheets

(56) References Cited

U.S. PATENT DOCUMENTS

| | | | |
|---|---|---|---|
| 8,805,489 | B1 | 8/2014 | Ofek |
| 2001/0049480 | A1* | 12/2001 | John et al. .................. 600/559 |
| 2006/0101079 | A1 | 5/2006 | Morikawa et al. |
| 2007/0191727 | A1 | 8/2007 | Fadem |
| 2008/0033317 | A1 | 2/2008 | Elberling |
| 2009/0147148 | A1 | 6/2009 | Morikawa et al. |
| 2010/0094162 | A1 | 4/2010 | Benasich et al. |
| 2011/0313309 | A1 | 12/2011 | Nicol et al. |
| 2012/0072213 | A1 | 3/2012 | Adachi et al. |

FOREIGN PATENT DOCUMENTS

| | | |
|---|---|---|
| JP | 06-114038 A | 4/1994 |
| JP | 09-038069 A | 2/1997 |
| JP | 11-511367 T | 10/1999 |
| JP | 2004-275619 A | 10/2004 |
| JP | 2008-503261 T | 2/2008 |
| WO | 2005/001677 A1 | 1/2005 |
| WO | 2007/066440 A1 | 6/2007 |
| WO | 2010/056947 A1 | 5/2010 |
| WO | 2011/093005 A1 | 8/2011 |

OTHER PUBLICATIONS

Hosoi et al., "Hochouki Tekigokensa No Shishin 2008", or "2008 Guidelines for Hearing Aid Suitability Test", 2008 and concise explanation.
Office Action for co-pending U.S. Appl. No. 12/959,513 dated Aug. 16, 2013.
Current claims for co-pending U.S. Appl. No. 12/959,513 submitted in response to Aug. 16, 2013 Office Action on Oct. 17, 2013.
Chinese search report for corresponding Chinese Application No. 201180011703.9, dated Jul. 2, 2014.
English translation of Search report for corresponding Chinese Application No. 201180011703.9, dated Jul. 2, 2014.
Co-pending U.S. Appl. No. 13/561,336 filed Jul. 30, 2012.
International Search Report for corresponding International Application No. PCT/JP2011/003237 mailed Sep. 20, 2011.
Form PCT/ISA/237 for corresponding International Application No. PCT/JP2011/003237 dated Sep. 20, 2012 and partial English translation.
International Search Report for related International Application No. PCT/JP2011/003236 mailed Sep. 20, 2011.
Form PCT/ISA/237 for related International Application No. PCT/JP2011/003236 dated Sep. 20, 2012 and partial English translation.
Kazuoki Kodera, "Hochoki Fittingu No Kangaekata" (or "Concept of Hearing Aid Fitting"), Shindan to Chiroysha, 1999, p. 166 and concise explanation (cited in [0006] of the specification).
"Jishoukanrendeni (ERP) Manyuaru-P300 Wo Chushinni" (or "Event-Related Potential (ERP) Manual-mainly concerning P300"), edited by Kimitaka Kaga et al., Shinohara Shuppan Shinsha, 1995, p. 30. and concise explanation (cited in [0164] of the specification).
Kazuoki Kodera, "Hochoki Fittingu No Kangaekata" (or "Concept of Hearing Aid Fitting"), Shindan to Chiryosha, 1999, p. 172 and concise explanation (cited in [0199] of the specification).
Tamesue et al., "Kiokuseishinsagyojino Souonnitaisuru Shinriseiritekiteiryohyokanikansuru Kisotekikousatsu (or "A Basic Discussion of Pyschological/Physiological Quantitative Evaluations with respect to Noises at Memorization Mental Tasks")", the Acoustical Society of Japan, a CD-ROM of spring research meeting preprints, 2009.03, pp. 1031-1032 and concise explanation.
S. Kuriki, "Measurements of Auditory Evoked Neuromagnetic Field Using a Multichannel SQUID Magnetometer", Journal of the Acoustical Society of Japan, May 1992, vol. 48, No. 5, pp. 320-327 and concise explanation.
Näätänen et al., "The N1 Wave of the Human Electric and Magnetic Response to Sound: A Review and an Analysis of the Component Structure", Psychophysiology, 24, 375-425 (1987).
Hisanaga et al., Shichokakuonseis Horino Nichi•Ei Bogokan ERP Hikaku (or "ERP Comparison Between Mother Tongues of Japanese/English in Visual and Auditory Speech Processing"), the Acoustical Society of Japan, a CD-ROM of autumn research meeting preprints, Sep. 2009, pp. 567-570 and concise explanation.

* cited by examiner

|  |  | FLAT/DISTORTED ||
|  |  | FLAT | DISTORTED |
| --- | --- | --- | --- |
| SOUND PRES-SURE | LARGE | LF CONDITION 75−85dB | LD CONDITION 75−85dB |
|  | MIDDLE | MF CONDITION 60−65dB | MD CONDITION 60−65dB |
|  | SMALL | SF CONDITION 40−45dB | SD CONDITION 40−45dB |

FIG.3A
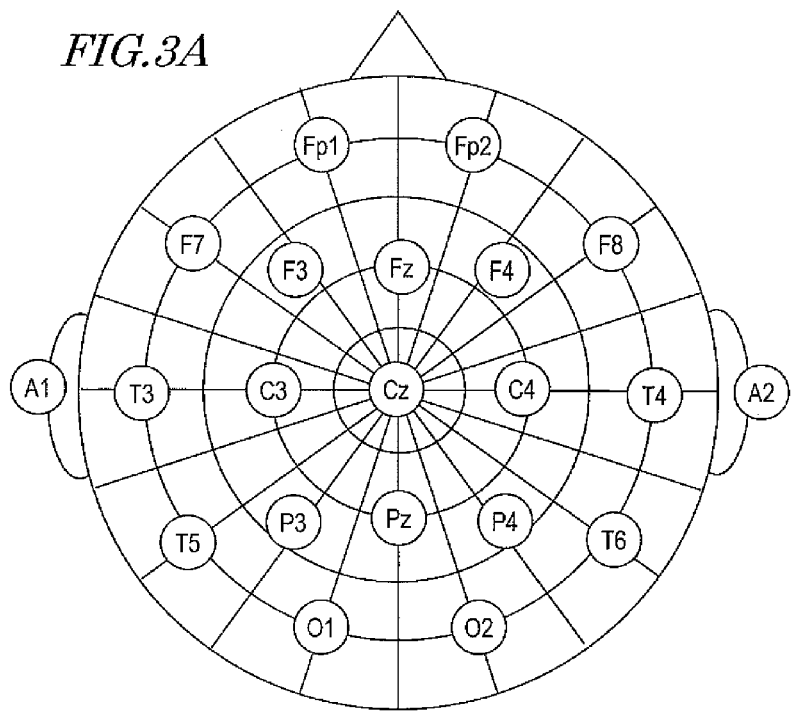
FIG.3B
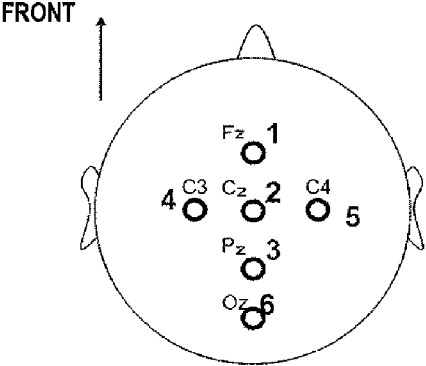
<UPPER VIEW>
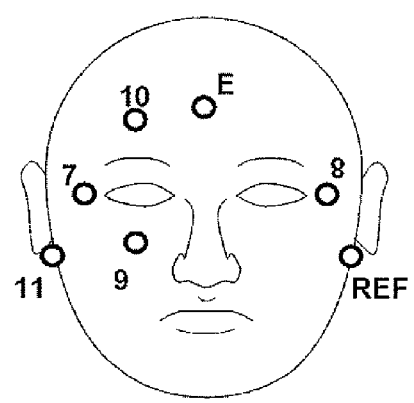
<FRONT VIEW>

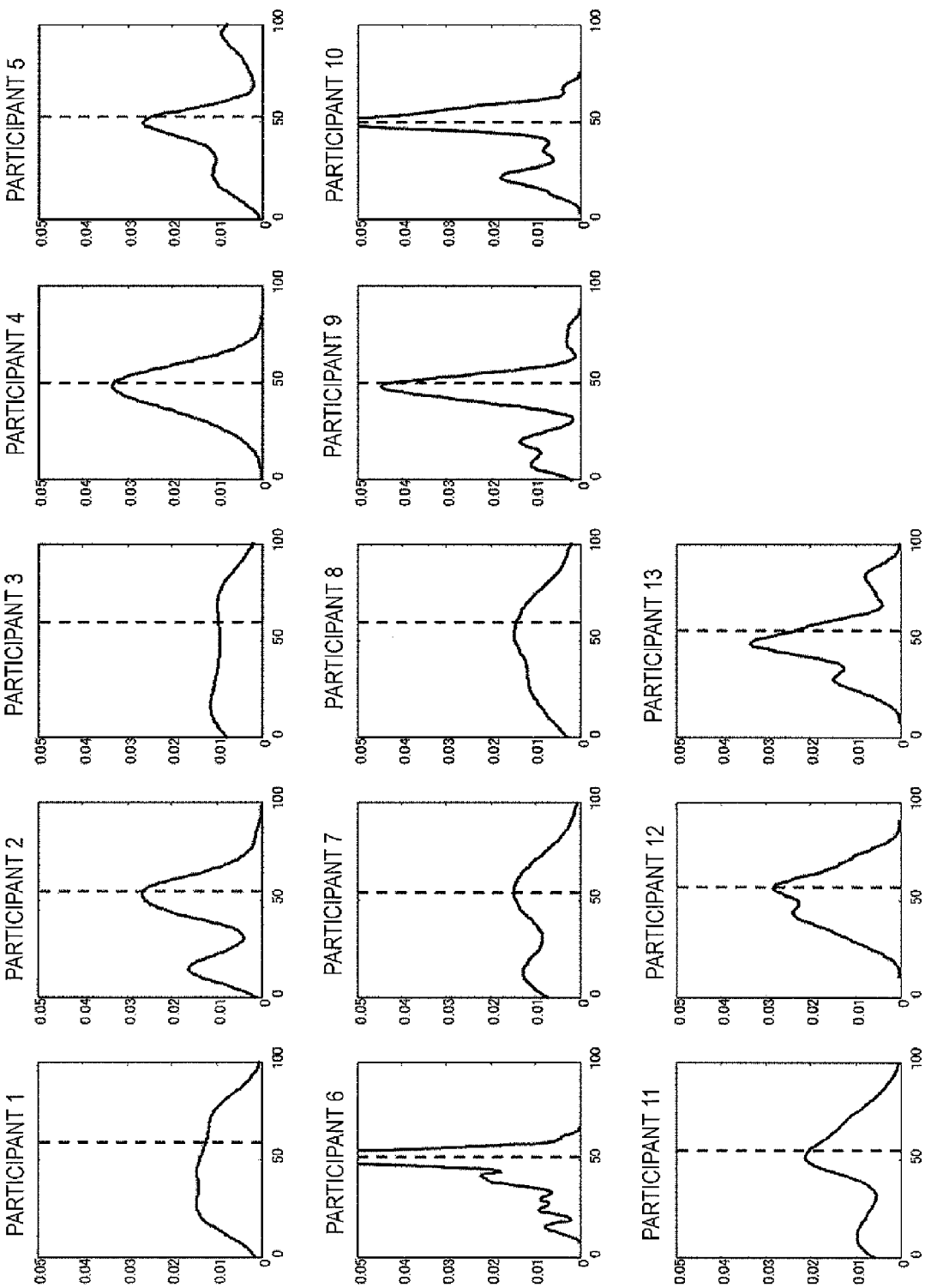

FIG.16

(a) STRIFE (b) ANNOYANCE

| ITEM OF DETERMINATION | DISTINCTION RATIO (REQUIRED NUMBER OF SUMMATIONS) | RESOLUTION OF DETERMINATION RESULT |
|---|---|---|
| INTELLIGIBILITY | HIGH (SMALL) | EACH SPEECH SOUND |
| COMFORTABLE-NESS | LOW (LARGE) | GROUPING POSSIBLE |

FIG.21

| SPEECH SOUND | AUDIO FILE | CONSONANT LABEL | GROUP | | | | | |
|---|---|---|---|---|---|---|---|---|
| | | | LIKELIHOOD OF CONFUSION | | | COMFORTABLENESS ASSESSMENT | | |
| | | | ROUGH CATEGOR | MEDIUM CATEGOR | FINE CATEGOR | ANNOYANCE | STRIFE | ... |
| a | a.wav | — | 0 | — | — | 1 | 1 | ... |
| u | u.wav | — | 0 | — | — | 3 | 1 | ... |
| o | o.wav | — | 0 | — | — | 5 | 1 | ... |
| si | shi.wav | s | 1 | 1 | — | 2 | 2 | ... |
| su | su.wav | s | 1 | 1 | — | 3 | 2 | ... |
| ki | ki.wav | k | 1 | 2 | — | 2 | 3 | ... |
| ku | ku.wav | k | 1 | 2 | — | 3 | 3 | ... |
| ta | ta.wav | t | 1 | 2 | — | 1 | 3 | ... |
| te | te.wav | t | 1 | 2 | — | 4 | 3 | ... |
| to | to.wav | t | 1 | 2 | — | 5 | 3 | ... |
| ha | ha.wav | h | 1 | 2 | — | 1 | 4 | ... |
| yo | yo.wav | y | 2 | 1 | — | 5 | 5 | ... |
| ri | ri.wav | r | 2 | 1 | — | 2 | 5 | ... |
| wa | wa.wav | w | 2 | 1 | — | 1 | 5 | ... |
| ni | ni.wav | n | 2 | 2 | 1 | 2 | 5 | ... |
| ne | ne.wav | n | 2 | 2 | 1 | 4 | 5 | ... |
| mo | mo.wav | m | 2 | 2 | 1 | 5 | 5 | ... |
| ga | ga.wav | g | 2 | 2 | 2 | 1 | 4 | ... |
| ji | ji.wav | j | 2 | 2 | 2 | 2 | 5 | ... |
| ba | ba.wav | b | 2 | 2 | 2 | 1 | 5 | ... |

FIG.27

DETERMINATION RESULT:

| ITEM OF DETERMINA-TION | a | ki | si | ta | ni | ... | ga |
|---|---|---|---|---|---|---|---|
| INTELLIGI-BILITY | ○ | × | ○ | ○ | × | ... | ○ |

| ITEM OF DETERMINA-TION | VOWEL (3 SPEECH SOUNDS) | | | VOICED CONSONANT (9 SPEECH SOUNDS) | | | UNVOICED CONSONANT (8 SPEECH SOUNDS) | | |
|---|---|---|---|---|---|---|---|---|---|
| | a | u | o | ni | ... | ga | ki | ... | to |
| COMFOR-TABLENESS | ○ | | | × | | | × | | |

FIG.28

| ITEM OF DETERMINA-TION | VOWEL (4 SPEECH SOUNDS) | | | | VOICED CONSONANT (9 SPEECH SOUNDS) | | | UNVOICED CONSONANT (8 SPEECH SOUNDS) | | |
|---|---|---|---|---|---|---|---|---|---|---|
| | a | a | u | o | ni | ... | ga | ki | ... | to |
| COMFOR-TABLENESS | ○ | | | | ○ | | | ○ | | |

FIG.29

| WORD | STRIFE | ANNOYANCE | INTELLIGIBILITY DETERMINATION | FACTOR OF UNCLEARNESS |
|---|---|---|---|---|
| sit | 1 | 0 | ○ | - |
| meet | 1 | 0 | ○ | - |
| get | 0 | 1 | ○ | - |
| cat | 0 | 1 | ○ | - |
| come | 1 | 0 | ○ | - |
| hot | 0 | 0 | ○ | - |
| law | 0 | 0 | ○ | - |
| book | 1 | 1 | ○ | - |
| blue | 1 | 1 | △ | INSUFFICIENT CONSONANT FREQUENCY GAIN |
| urge | 0 | 0 | ○ | - |
| star | 0 | 0 | △ | INSUFFICIENT CONSONANT FREQUENCY GAIN |
| page | 0 | 1 | ○ | - |
| sky | 1 | 1 | △ | INSUFFICIENT SOUND PRESSURE |
| join | 0 | 0 | ○ | - |
| now | 0 | 1 | ○ | - |
| home | 1 | 1 | ○ | - |
| here | 1 | 1 | △ | INSUFFICIENT CONSONANT FREQUENCY GAIN |
| care | 0 | 0 | ○ | - |
| ... | ... | ... | ... | ... |

FIG.33

| AMOUNT OF AMPLIFICATION (dB) |
|---|
| 5dB |
| 10dB |
| 15dB |
| 20dB |

| ADDITIONAL AUDIO FUNCTION | ON／OFF |
|---|---|
| DIRECTIVITY LEVEL | ON |
| CONSONANT EMPHASIS | OFF |
| NOISE REDUCTION | OFF |
| ... | ... |

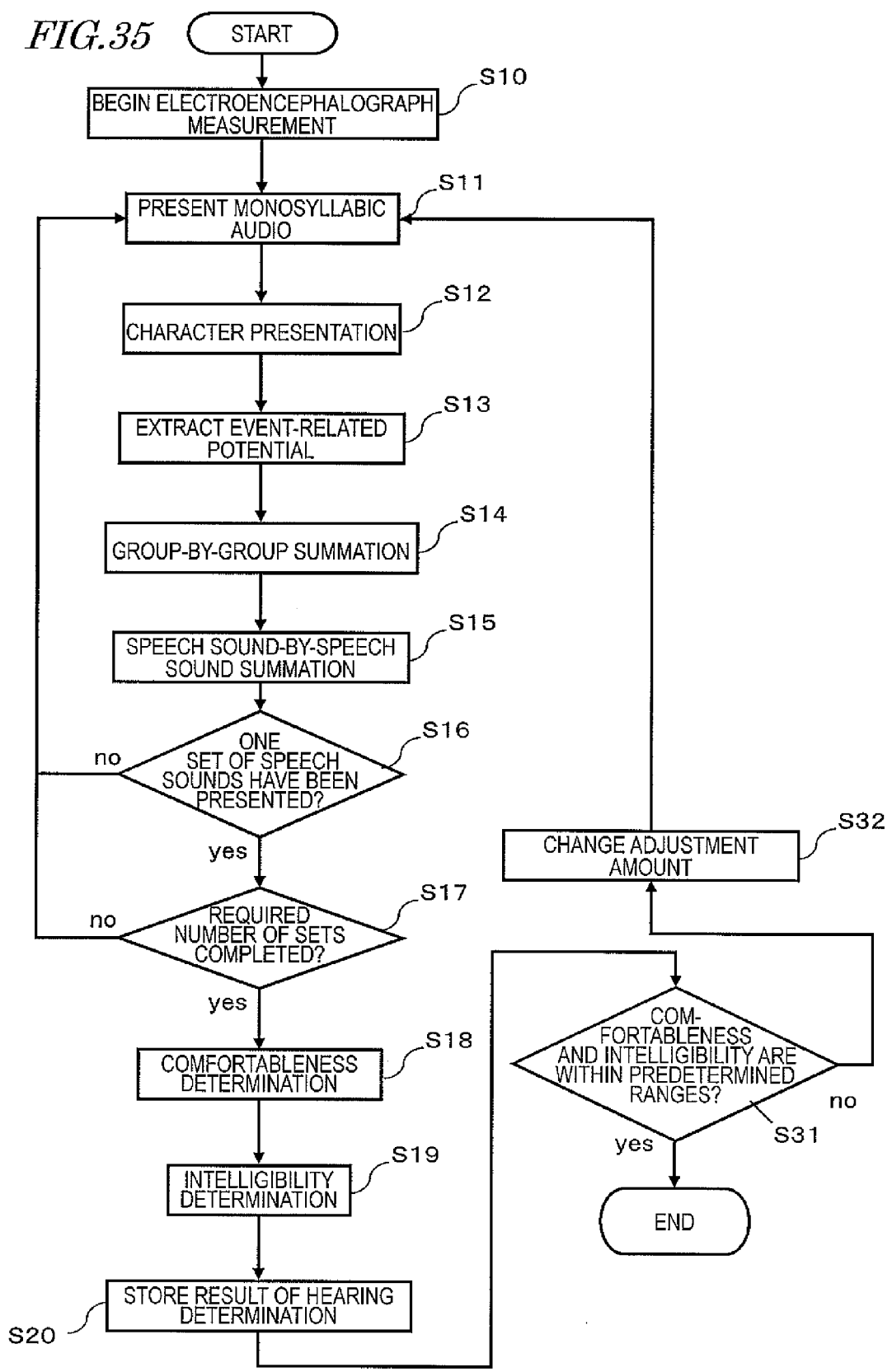

HEARING DETERMINATION SYSTEM, AND METHOD AND PROGRAM FOR THE SAME

This is a continuation of International Application No. PCT/JP2011/003237, with an international filing date of Jun. 8, 2011, which claims priority of Japanese Patent Application No. 2010-134240, filed on Jun. 11, 2010, the contents of which are hereby incorporated by reference.

BACKGROUND

1. Technical Field

The present application relates to a technique of determining whether a speech sound has been aurally comprehended or not, and whether a speech sound has been heard in comfort. More specifically, the present application relates to a hearing determination system which simultaneously determines speech sound intelligibility and comfortableness, for the "fitting" of a hearing aid or the like to provide a sound of appropriate loudness for each individual user by adjusting the amount of amplification, etc., of sounds with respect to each frequency.

2. Description of the Related Art

In recent years, people suffering from presbycusis are increasing in number due to the aging society. Even among the young, due to increased opportunities for listening to loud music for long hours as well as other influences, there is an increasing number of people suffering from hypacusia associated with acoustic traumas. Moreover, due to the downsizing and improved performance of hearing aids, users feel less of a psychological barrier against wearing hearing aids. Against this background, there is an increasing number of users of hearing aids.

A hearing aid is a device for amplifying sounds of frequencies which are difficult for a user to aurally distinguish. The purpose of wearing a hearing aid is to provide an improved aural distinction ability in conversation by compensating for deteriorated hearing of a user. The amount of sound amplification which a user desires in a hearing aid varies depending on the level of deterioration in the hearing of the user. Therefore, before beginning use of a hearing aid, it is first necessary to conduct a hearing determination for each user.

Within the realm of hearing determination required prior to using a hearing aid, determination of speech sound intelligibility is of importance. "Determination of speech sound intelligibility" means a determination as to whether a speech sound has been aurally comprehended or not. Specifically, it pertains to a determination of an aural distinction ability as to whether a monosyllabic speech sound has been aurally comprehended or not. A "monosyllabic speech sound" is either a single vowel or a combination of a consonant and a vowel (e.g., "あ (a)"/"だ (da)"/"し (shi)").

According to "HOCHOKI FITTINGU NO KANGAEKATA (or "Concept of Hearing Aid Fitting"), Kazuoki KODERA, Shindan To Chiryosha, 1999, p. 166), conventional determination of speech sound intelligibility has been performed through the following procedure. First, by using the 57S list (50 monosyllables) or the 67S list (20 monosyllables) proposed by the Japan Audiological Society, a user is allowed to hear monosyllabic audios, one by one, the audios being presented orally or by playing back a CD. Next, through oral explanation, writing, or other methods, the user is asked to answer which speech sound he or she has aurally comprehended the presented speech sound to be. Then, a person making the determination matches the answer against the list, and calculates a correctness rate, which is a rate of monosyllables that have been correctly aurally comprehended among all monosyllables. This correctness rate defines the speech sound intelligibility. As for methods of speech sound intelligibility determination, techniques described in Japanese Laid-Open Patent Publication No. 9-038069 and Japanese Laid-Open Patent Publication No. 6-114038 are known.

SUMMARY

The prior art technique needs further improvement in view of a time for determining comfortableness when a speech sound is heard, or for determining speech sound intelligibility and comfortableness.

One non-limiting, and exemplary embodiment provides a technique to provide a hearing determination system for determining comfortableness when a speech sound is heard, the determination being made in a short period of time. Furthermore, another one non-limiting, and exemplary embodiment provides a technique to provide a hearing determination system for determining speech sound intelligibility and comfortableness at the same time and in a short period of time.

In one general aspect, a hearing determination system disclosed herein according to the present disclosure is a determination system comprising: a biological signal measurement section configured to measure an electroencephalogram signal of a user; a presented-speech sound control section configured to determine a speech sound to be presented to the user, by referring to a speech sound database retaining data of a plurality of speech sounds and data defining at least one group within the plurality of speech sounds; an auditory stimulation presentation section configured to present the determined speech sound to the user as an audio; a visual stimulation presentation section configured to present the determined speech sound to the user as a character; a groupwise summation section configured to, by referring to the speech sound database, take a summation of an event-related potential of the electroencephalogram signal for each group of speech sounds; a first determination section configured to, from the event-related potential having been subjected to summation for each group, make a group-by-group determination of comfortableness as to whether the user is comfortably hearing the speech sound and outputting a determination result; and an second determination section configured to, from the event-related potential, make a speech sound-by-speech sound determination of intelligibility as to whether the user is clearly hearing the speech sound and outputting a determination result.

According to the present disclosure, when an event-related potential with respect to presentation of an audio of a monosyllabic speech sound and an event-related potential with respect to presentation of a character are measured, different portions of the electroencephalogram waveform are selected for summation respective for speech sound intelligibility determination and comfortableness determination, whereby the numbers of audio and character presentations can be reduced. As a result, hearing determination based on the electroencephalogram can be achieved in a short period of time, whereby a hearing determination which presents little burden to the user can be realized.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 3A is a diagram showing electrode positions according to the International 10-20 system, and FIG. 3B is a diagram showing electrode positioning as to how electrodes are worn in the present experiments.

FIG. 7 is a diagram showing results of subjective determination of different participants concerning annoyance.

FIG. 16 is a diagram showing an exemplary grouping of the 20 speech sounds in the 67S list.

FIG. 21 is a diagram showing an exemplary database stored in a speech sound DB 12.

FIG. 27 is a diagram showing exemplary results of intelligibility determination, and, exemplary results of comfortableness determination for different groups into which speech sounds are classified.

FIG. 28 is a diagram showing results of comfortableness determination for different groups into which speech sounds are classified, where a speech sound of a certain group (vowel "ア (a)") is repeated.

FIG. 29 is a diagram showing exemplary results of determining strife, annoyance, and intelligibility for different monosyllabic words.

FIG. 33 is a diagram showing exemplary data stored in an adjustment amount DB 301.

FIG. 34 is a diagram showing exemplary information with which to adjust acoustic aiding processes, the information being stored in the adjustment amount DB 301.

FIG. 35 is a flowchart showing an overall processing procedure which is performed in the hearing aid adjustment system 103.

DETAILED DESCRIPTION

Figure 1:
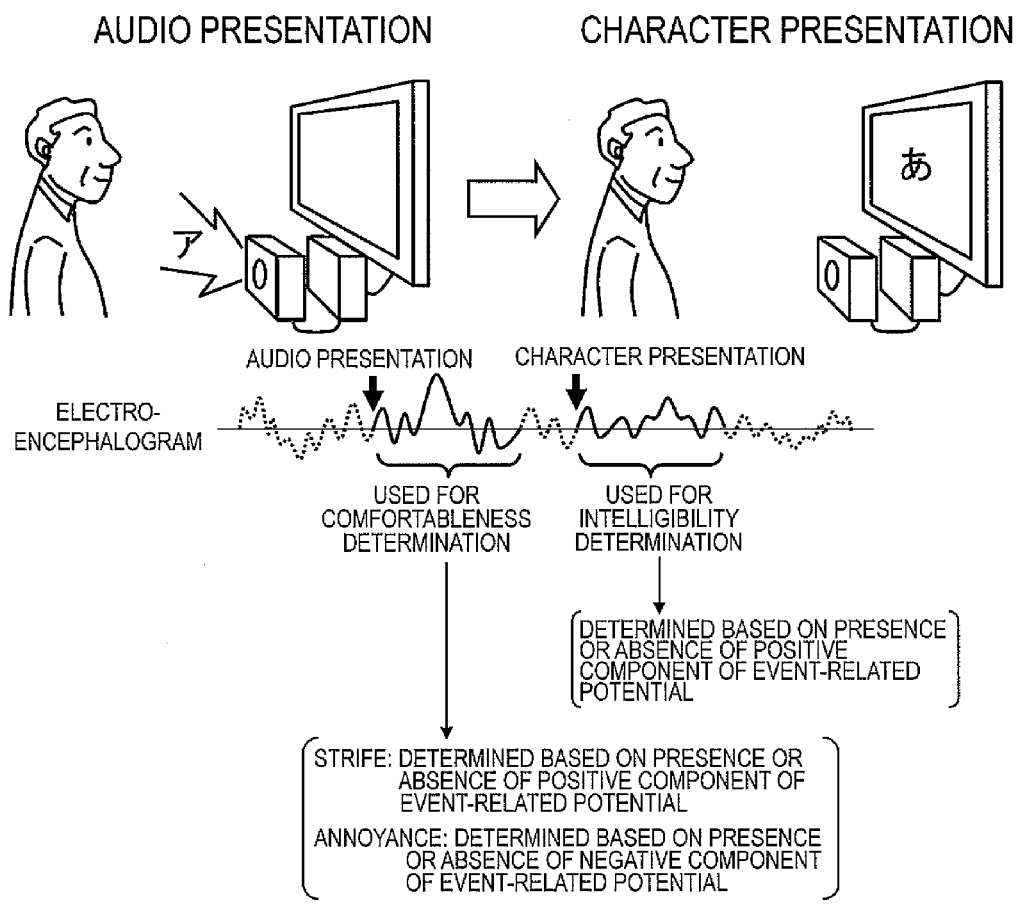
FIG. 1 is a diagram showing, in a hearing determination system according to the present disclosure, an electroencephalogram which is utilized when making a comfortableness determination and an intelligibility determination, as well as timing of audio presentation and character presentation.

In the aforementioned determination method of the related art, the user is required to answer via oral explanation or writing, and the person making the determination needs to go through manual labor in determining the correctness of the user's answer. Thus, the aforementioned determination method presents a large burden, and is time-consuming, on the part of the user and the person making the determination.

On the other hand, when a long-time use of a hearing aid is envisaged, not only the speech sound intelligibility but also the comfortableness when the hearing aid is being worn needs to be determined. "Comfortableness determination" means a determination as to whether the user is listening in comfort.

Conventional determinations of comfortableness have been made from the standpoint of whether the user is in an uncomfortable state or not. For example, the user would orally tell the person making the determination if he or she finds the sound to be annoying beyond tolerance or if the sound is too soft to hear. Alternatively, an uncomfortable level check for determining a maximum output sound pressure level would be made. With these, it is difficult to make an objective determination as to how comfortably the user is listening to a sound.

In view of the above, a hearing determination system according to the present disclosure is a determination system comprising: a biological signal measurement section configured to measure an electroencephalogram signal of a user; a presented-speech sound control section configured to determine a speech sound to be presented to the user, by referring to a speech sound database retaining data of a plurality of speech sounds and data defining at least one group within the plurality of speech sounds; an auditory stimulation presentation section configured to present the determined speech sound to the user as an audio; a visual stimulation presentation section configured to present the determined speech sound to the user as a character; a group-wise summation section configured to, by referring to the speech sound database, take a summation of an event-related potential of the electroencephalogram signal for each group of speech sounds; a first determination section configured to, from the event-related potential having been subjected to summation for each group, make a group-by-group determination of comfortableness as to whether the user is comfortably hearing the speech sound and outputting a determination result; and an second determination section configured to, from the event-related potential, make a speech sound-by-speech sound determination of intelligibility as to whether the user is clearly hearing the speech sound and outputting a determination result.

The first determination section may make a group-by-group determination of comfortableness based on whether the event-related potential having been subjected to summation for each group has a predetermined positive component in a range from 600 ms to 900 ms based on a point in time at which the audio of the speech sound is presented by the auditory stimulation presentation section as a starting point, and has a predetermined negative component in a range from 100 ms to 300 ms.

The first determination section may include: a positive component determination section configured to determine whether the event-related potential having been subjected to summation for each group has a predetermined positive component in a range from 600 ms to 900 ms based on the point in time at which the audio of the speech sound is presented by the auditory stimulation presentation section as a starting point; a negative component determination section configured to determine whether the user is comfortably hearing the speech sound based on whether the event-related potential having been subjected to summation for each group has a predetermined negative component in a range from 100 ms to 300 ms based on the point in time at which the audio of the speech sound is presented by the auditory stimulation presentation section as a starting point; and a determination section configured to make a group-by-group determination of comfortableness based on a determination result by the positive component determination section and a determination result by the negative component determination section.

The intelligibility determination section may make a speech sound-by-speech sound determination of intelligibility based on whether the event-related potential having been subjected to summation for each speech sound has a predetermined positive component in a range from 200 ms to 400 ms or a range from about 400 ms to 600 ms based on a point in time at which the character of the speech sound is presented by the visual stimulation presentation section as a starting point.

In the speech sound database, each of the plurality of speech sounds may be categorized into the at least one group based on a predetermined rule.

The at least one group may include a vowel group, a voiced consonant group, and an unvoiced consonant group.

In the speech sound database, each of the plurality of speech sounds may be categorized into the at least one group based on a magnitude of probability of confusion.

The presented-speech sound control section may determine a number of presentations by which the speech sound is to be presented to the user; in the speech sound database, each of the plurality of speech sounds may be categorized into the at least one group based on a number of speech sounds; and in accordance with the number of speech sounds of the at least one group, the presented-speech sound control section may determine a number of presentations by which the audio is to be presented by the auditory stimulation presentation section and a number of presentations by which the character is to be presented by the visual stimulation presentation section.

The presented-speech sound control section may determine a number of presentations by which the speech sound is to be presented to the user; and the auditory stimulation presentation section and the visual stimulation presentation section may continue to present the audio and character of the speech sound until the number of presentations for the audio and the number of presentations for the character as determined by the presented-speech sound control section are reached.

The presented-speech sound control section may determine a number of presentations by which the speech sound is to be presented to the user; and the presented-speech sound control section may determine that a specific speech sound is to be presented to the user a plurality of times.

The presented-speech sound control section may determine the number of presentations based on a level of the electroencephalogram signal of the user.

The hearing determination system may further comprise a hearing determination result database configured to store determination results output from the comfortableness determination section and the intelligibility determination section.

The hearing determination system may further comprise a speech sound-wise summation section configured to take a summation of the event-related potential for each speech sound by referring to the speech sound database, wherein from the event-related potential having been subjected to summation for each speech sound, the intelligibility determination section makes a speech sound-by-speech sound determination of intelligibility as to whether the user is clearly hearing the speech sound.

Another determination system according to the present disclosure comprises: a biological signal measurement section configured to measure an electroencephalogram signal of a user; a presented-speech sound control section configured to determine a speech sound to be presented to the user, by referring to a speech sound database retaining data of a plurality of speech sounds and data defining at least one group within the plurality of speech sounds; an auditory stimulation presentation section configured to present the determined speech sound to the user as an audio; a group-wise summation section configured to, by referring to the speech sound database, take a summation of an event-related potential of the electroencephalogram signal for each group of speech sounds; and a comfortableness determination section configured to, from the event-related potential having been subjected to summation for each group, make a group-by-group determination of comfortableness as to whether the user is comfortably hearing the speech sound and outputting a determination result.

Still another determination system according to the present disclosure comprises: a presented-speech sound control section configured to determine a speech sound to be presented to a user by referring to a speech sound database retaining data of a plurality of speech sounds and data defining at least one group within the plurality of speech sounds, and to control an auditory stimulation presentation section to present the determined speech sound to the user as an audio and to control a visual stimulation presentation section to present the determined speech sound to the user as a character; a group-wise summation section configured to, by referring to the speech sound database, take a summation of an event-related potential of an electroencephalogram signal of the user measured by a biological signal measurement section for each group of speech sounds; a comfortableness determination section configured to, from the event-related potential having been subjected to summation for each group, make a group-by-group determination of comfortableness as to whether the user is comfortably hearing the speech sound and outputting a determination result; and an intelligibility determination section configured to, from the event-related potential, make a speech sound-by-speech sound determination of intelligibility as to whether the user is clearly hearing the speech sound and outputting a determination result.

A hearing determination method according to the present disclosure comprises the steps of: measuring an electroencephalogram signal of a user; determining a speech sound to be presented to the user, by referring to a speech sound database retaining data of a plurality of speech sounds and data defining at least one group within the plurality of speech sounds; presenting a speech sound determined by the step of determining to the user as an audio; presenting a speech sound determined by the step of determining to the user as a character; by referring to the speech sound database, taking a summation of an event-related potential of the electroencephalogram signal for each group of speech sounds; from the event-related potential having been subjected to summation for each group, making a group-by-group determination of comfortableness as to whether the user is comfortably hearing the speech sound and outputting a determination result; and from the event-related potential, making a speech sound-by-speech sound determination of intelligibility as to whether the user is clearly hearing the speech sound and outputting a determination result.

A computer program according to the present disclosure is a computer program stored on a non-transitory computer-readable medium, and to be executed by a computer mounted in a hearing determination system, wherein the computer program causes the computer in the hearing determination system to execute the steps of: receiving an measured electroencephalogram signal of a user; determining a speech sound to be presented to the user, by referring to a speech sound database retaining data of a plurality of speech sounds and data defining at least one group within the plurality of speech sounds; presenting the determined speech sound to the user as an audio; presenting the determined speech sound to the user as a character; by referring to the speech sound database, taking a summation of an event-related potential of the electroencephalogram signal for each group of speech sounds; from the event-related potential having been subjected to summation for each group, making a group-by-group determination of comfortableness as to whether the user is comfortably hearing the speech sound and outputting a determination result; and from the event-related potential, making a speech sound-by-speech sound determination of intelligibility as to whether the user is clearly hearing the speech sound and outputting a determination result.

According to the present disclosure, when an event-related potential with respect to presentation of an audio of a monosyllabic speech sound and an event-related potential with respect to presentation of a character are measured, different portions of the electroencephalogram waveform are selected for summation respective for speech sound intelligibility determination and comfortableness determination, whereby the numbers of audio and character presentations can be reduced. As a result, hearing determination based on the electroencephalogram can be achieved in a short period of time, whereby a hearing determination which presents little burden to the user can be realized.

Moreover, according to the present disclosure, comfortableness determination is performed by using an event-related potential with respect to audio presentation of a monosyllabic speech sound. By not performing speech sound intelligibility determination, hearing determination (especially comfortableness determination) is enabled in a shorter period of time.

Hereinafter, embodiments of a hearing determination system according to the present application will be described with reference to the drawings.

The hearing determination system according to the present application is used, where a user state when listening to a speech sound is separately considered with respect to whether the speech sound has been aurally distinguished and how comfortably the user has listened to the speech sound, for determining the user state based on an electroencephalogram. For example, as shown in FIG. 1, the hearing determination system may combine comfortableness determination and speech sound intelligibility determination. However, only a comfortableness determination may be made, without making a speech sound intelligibility determination.

Comfortableness determination is to be made, on the premise of presenting a monosyllabic speech sound in the form of an audio and asking the user to aurally distinguish the audio, by utilizing as an index an event-related potential of the user electroencephalogram signal based on the audio presentation as a starting point. Speech sound intelligibility determination is to be made, on the premise of presenting a monosyllabic speech sound in the form of an audio and thereafter presenting a text character and then asking the user to determine whether the presented audio matches the presented character, by utilizing as an index an event-related potential of the user electroencephalogram signal based on the character presentation as a starting point. As used herein, an "event-related potential" means a portion of an electroencephalogram, referring to a transient potential fluctuation in the brain which occurs in temporal relationship with an external or internal event.

The present specification illustrates that determinations of comfortableness and speech sound intelligibility can be made based on event-related potentials of an electroencephalogram. Firstly, electroencephalogram measurement experiments which were conducted by the inventors in order to study what electroencephalogram components enable comfortableness determination and speech sound intelligibility determination will be described in detail, followed by the description of embodiments.

1. Experiment Conducted by the Inventors

The inventors believe that not only speech sound intelligibility determination but also comfortableness determination is necessary. Through the subsequently-described experiments, the inventors have arrived at the concept that comfortableness determination can be separated into the two factors of: (1) "strife" concerning how much effort has been made to aurally distinguish a speech sound; and (2) "annoyance" indicating how annoying (i.e., loud) a speech sound has been felt as. This concept is unprecedentedly obtained through a detailed analysis of the user state at the time of measuring a below-described speech sound intelligibility curve, as will be specifically described below.

In a speech sound intelligibility determination, a ◯/X determination is made as to whether each speech sound was aurally distinguished, and the number of speech sounds that have been successfully aurally distinguished is divided by the number of speech sounds subjected to determination (i.e., 20 in the case of the 67S list). The "speech sound intelligibility curve" mentioned above is a curve indicating a result of measuring this speech sound intelligibility at a plurality of hearing levels. Since a determination result which is obtained through a speech sound intelligibility determination indicates a correctness rate of aural distinction, the result reflects whether aural distinction has been correctly made, but does not reflect any user state when listening to speech sounds. However, among situations where aural distinction has been correctly made, there may be cases where the aural distinction was made in comfort as well as cases where the aural distinction was made in discomfort.

A speech sound intelligibility determination is a short-time determination which takes place at a hearing aid shop, and therefore a user under determination will try to aurally distinguish speech sounds with maximum strife. Moreover, the fact as to whether the user feels annoyed or not is irrelevant to the determination; therefore, unless it is so annoying that it is intolerable, the user will be willing to carry out the determination task even if slightly annoyed. In the case where a hearing aid is worn on a daily basis, it would be difficult to always maintain maximum strife to try to aurally comprehend conversations. Since the hearing aid is to be worn for a long time, tolerating annoyance for the long time would be a burden to the user.

In view of these situations, the inventors have arrived at the thought that determination needs to be made separately with respect to different user states when listening to speech sounds: when neither strife nor patience for annoyance is needed; and when some strife or patience for annoyance is needed. Thus, the inventors have identified these to be factors of comfortableness at speech sound listening. Since strife and annoyance pertain to entirely distinct processes in the brain, there is a possibility that these can be separately determined through electroencephalogram measurement.

Accordingly, the inventors have conducted the following two experiments in order to identify electroencephalogram characteristic components for realizing speech sound intelligibility determination and comfortableness determination.

First, on the premise of presenting a monosyllabic speech sound in the form of an audio and asking the user to think of a speech sound corresponding to the audio, an electroencephalogram measurement experiment was conducted to measure an event-related potential based on the audio presentation as a starting point, in which subjective reports on "strife" and "annoyance" were subsequently made to define comfortableness concerning the speech sound (Electroencephalogram measurement experiment 1).

Furthermore, on the premise of presenting a monosyllabic speech sound sequentially in the form of an audio and a character, an electroencephalogram measurement experiment was conducted to measure an event-related potential based on the character presentation as a starting point (Electroencephalogram measurement experiment 2).

In Electroencephalogram measurement experiment 1, based on subjective reports on strife/annoyance, an arithmetic mean of event-related potentials for each element was taken. In Electroencephalogram measurement experiment 2, based on subjective reports on annoyance acquired before and after the experiment, an arithmetic mean of event-related potentials was taken. In Electroencephalogram measurement experiment 2, an arithmetic mean of event-related potentials was taken based on matching/mismatching between audios and characters as acquired during the experiment.

The results of the above two event-related potential experiments are summarized below.

The results of Electroencephalogram measurement experiment 1 indicated, in the event-related potential based on audio stimulation as a starting point, that: when there is high confidence of aural distinction of the audio, a positive component is induced at the parietal at a latency of about 750 ms, as compared to when there is high confidence of aural distinction of the audio.

It was also indicated that, independently from the aforementioned positive component, the amplitude of a negative component at a latency of about 200 ms increases with an increase in the sound pressure level of the stimulation audio.

The results of Electroencephalogram measurement experiment 2 indicated, in the event-related potential based on character stimulation as a starting point, that: when the audio is poorly aurally distinguished, a positive component is induced at the parietal at a latency of about 500 ms, as compared to when the audio is clearly aurally distinguished; and when the audio is clearly aurally distinguished, a positive component is induced at the parietal at a latency of about 300 ms, as opposed to when the audio is poorly aurally distinguished. As used herein, "latency" represents, based on the point in time of presenting an audio stimulation as a starting point, an amount of time which lapses before a positive component or negative component appears.

From these confirmations and findings, it has been found that: (1) a strife determination can be made by relying on the presence or absence of a positive component in an event-related potential at a latency of about 750 ms based on the point of presenting the audio as a starting point, from the correspondence with confidence of aural distinction of the audio; (2) an annoyance determination can be made by relying on the presence or absence of a negative component at a latency of about 200 ms; and (3) a speech sound intelligibility can be determined by relying on the presence or absence of a positive component at a latency of about 300 ms and a positive component at a latency of about 500 ms in an event-related potential, based on the point of presenting the character as a starting point. With this technique, simultaneously with speech sound intelligibility determination, determinations as to whether the user was striving and/or being annoyed when listening to the speech sound can be made in an objective and quantitative manner.

Hereinafter, the electroencephalogram measurement experiments which were conducted by the inventors in order to realize hearing determination will be described in detail.

1.1. Electroencephalogram Measurement Experiment 1 (Experiment Concerning Comfortableness)

In Electroencephalogram measurement experiment 1, relationship between subjective reports on strife and annoyance acquired after audio presentation and an event-related potential based on the audio as a starting point was examined. Hereinafter, with reference to FIG. 2 to FIG. 9, the experimental setting and experimental results of the electroencephalogram measurement experiment will be described.

Fifteen undergraduate and graduate students with normal hearing participated in the experiment.

From among unvoiced consonants which are supposed to induce mistakes in aural comprehension, 8 sounds (シ (shi), ス (su), キ (ki), ク (ku), タ (ta), テ (te), ト (to), ハ (ha)) in the 67S list as proposed by the Japan Audiological Society were selected as the speech sounds to be presented as stimulations. Speech sounds with adjusted frequency gains were used, thus to control the comfortableness factors of "strife" and "annoyance" for participants with normal hearing. A "frequency gain" refers to a gain (i.e., a circuit gain or rate of amplification) for each of a number of frequency bands.

For frequency gain adjustment, three sound pressure levels (Large, Middle, Small)×two distortion levels (Flat, Distorted) were set, totaling six conditions, as are detailed in (1) to (6) below. When labeling the conditions in the present specification, large sound pressure and flat (no distortion) conditions may be referred to as LF condition (an acronym of Large and Flat), for example.

(1) LF (Large Flat) condition: the gain was increased by 20 dB across entire frequency band, meant as an audio which had a large sound pressure and was easy to aurally distinguish. (2) LD (Large Distorted) condition: the gain was universally increased by 20 dB relative to the MD condition, meant as an audio which had a large sound pressure but was difficult to aurally distinguish. (3) MF (Middle Flat) condition: the frequency gain was not modified, meant as an audio which had a large sound pressure and was easy to aurally distinguish. (4) MD (Middle Distorted) condition: from an audio of the LF condition, the gain at frequencies of 250 Hz to 16 kHz was gradually adjusted (decreased) to −30 dB, meant as an audio which was difficult to aurally distinguish. (5) SF (Small Flat) condition: the gain was decreased by 20 dB across the entire frequency band, meant as an audio which had a small sound pressure but was easy to aurally distinguish. (6) SD (Small Distorted) condition: the gain was universally decreased by 20 dB relative to the MD condition, meant as an audio which had a small sound pressure and was difficult to aurally distinguish.

Figures 2A, 2B:
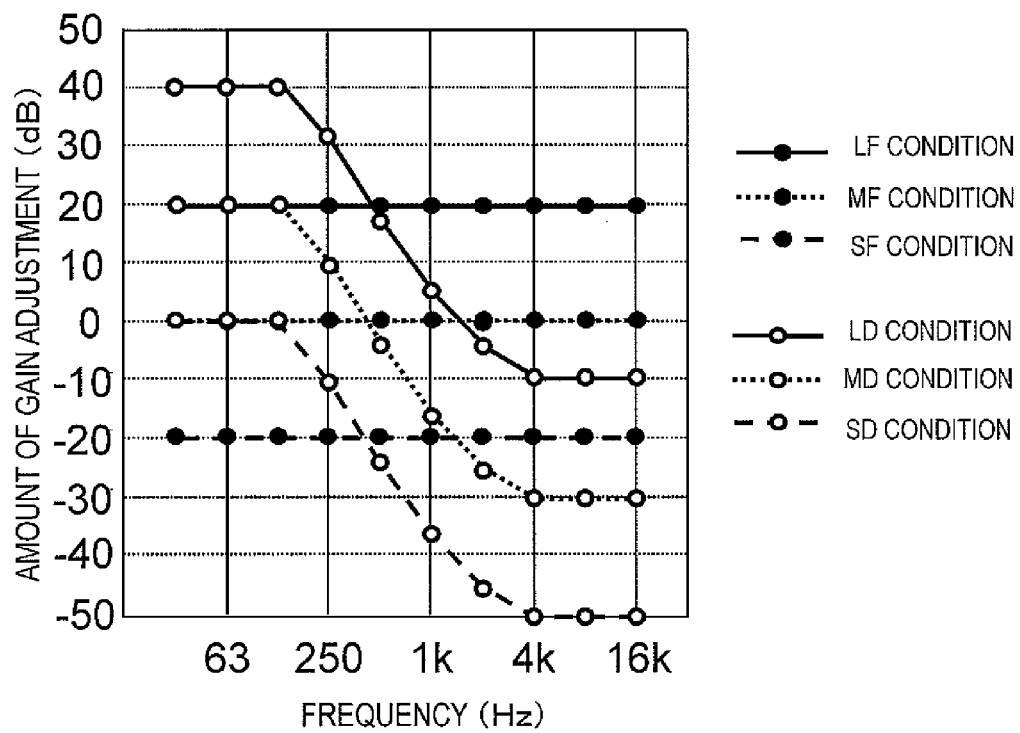
FIG. 2A is a diagram showing six conditions of audio and distortion.
FIG. 2B is a diagram showing amounts of gain adjustment for different frequencies.

FIG. 2A shows classification of six conditions concerning sound pressure level and distortion. FIG. 2B shows amounts of gain adjustment for different frequencies. The reason why the frequency gain for high frequencies was decreased is in order to reproduce a typical pattern of hypacusia of elderly people, i.e., gradual high tone loss. The audio stimulations were presented from a loudspeaker with flat frequency characteristics.

Each electroencephalogram was recorded from electrodes placed at the Fz, Cz, Pz, C3, and C4 (International 10-20 system) on the scalp, the right and left temples, and above and below the right eye, on the basis of the right mastoid. A "mastoid" is a protrusion of the cranium below the hind root of an ear. FIG. 3A shows electrode positions according to the International 10-20 system (10-20 System), whereas FIG. 3B shows electrode positioning as to how electrodes were worn in the present experiment. The sampling frequency was 200 Hz, and the time constant was 1 second. It was subjected to a 1 to 6 Hz digital band-pass filter off-line. As an event-related potential in response to an audio presentation, a waveform from −200 ms to 1000 ms was cut out based on the point of audio presentation as a starting point. Herein, "−200 milliseconds" signifies a point in time which is 200 milliseconds before the point of audio presentation.

Figure 4:
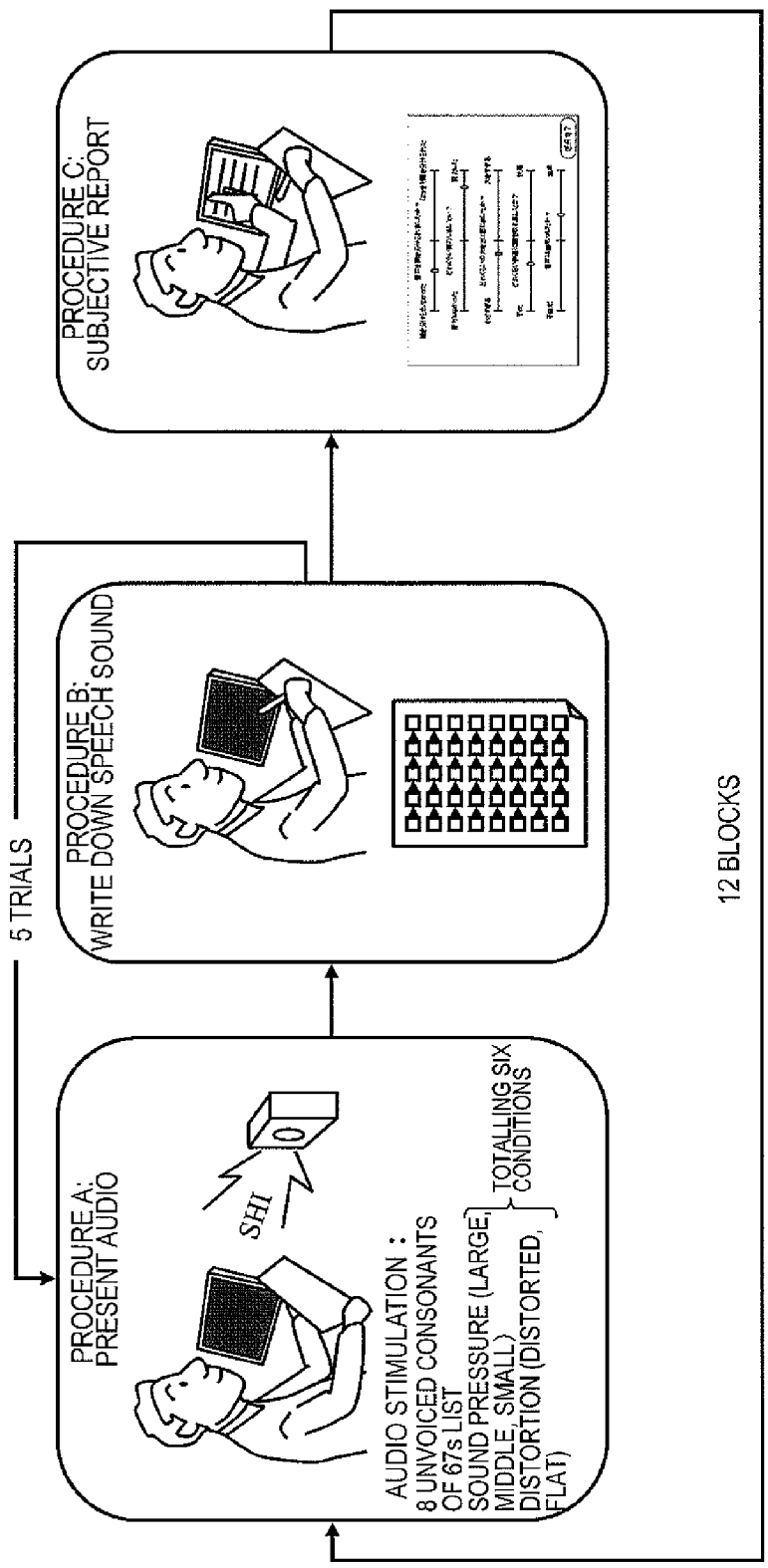
FIG. 4 is a diagram showing an experimental procedure of an electroencephalogram measurement experiment in outline.

FIG. 4 shows an experimental procedure of the electroencephalogram measurement experiment in outline. First, a monosyllabic audio, whose frequency gain had been adjusted according to one of the six conditions, was presented in Procedure A. The particulars of the presented audios will be described later. Next, in Procedure B, each participant was allowed to hear an audio, and asked to write down a character corresponding to the audio as he or she heard it. The conditions of the presented audios were kept unvaried, while only the speech sound type was varied. Procedures A and B were repeated five times (5 trials). Then, in Procedure C, the participant was asked to make a subjective determination concerning strife/annoyance and the like with respect to each audio that was presented in Procedure A. The subjective determination was based on a visual analog scale (100-step determination), and was made by using a touch panel. This was repeated 12 blocks, where 1 block consisted of Procedure A to Procedure C as above (totaling 60 trials). For each block, the sound pressure and distortion conditions of the presented audios were varied in random order.

Figure 5:
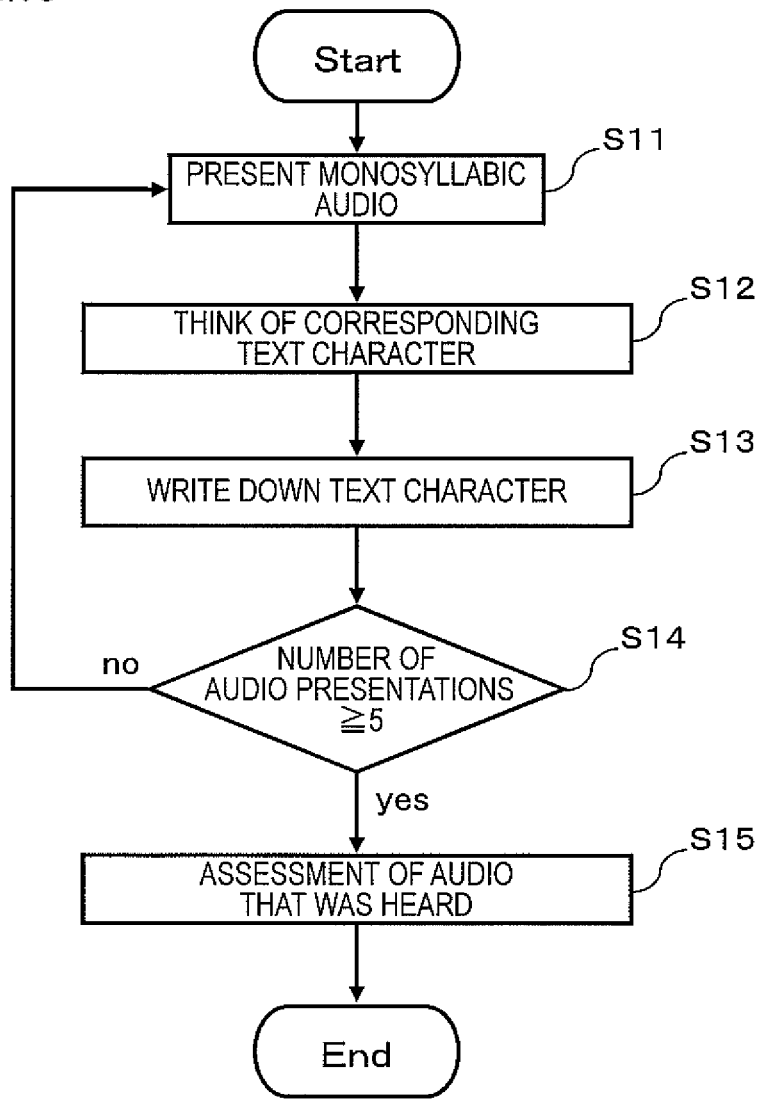
FIG. 5 is a flowchart showing a procedure corresponding to one trial.

FIG. 5 is a flowchart showing a procedure corresponding to one trial.

At step S11, a monosyllabic audio is presented to an experimental participant.

At step S12, the participant thinks of a corresponding text character upon hearing the monosyllabic audio.

At step S13, the participant writes down the text character corresponding to the audio as he or she heard it.

At step S14, the number of times that the audios have been presented is counted. While the number of presentations is equal to or less than 4, the process returns to S11. When the number of presentations reaches 5, the process proceeds to S15, where the number of presentations is reset.

At step S15, the participant answers with a subjective perception of the audio which was heard at step S11.

Hereinafter, distribution of results of subjective determination and threshold value setting will be described.

First, results of subjective determination will be described. Based on the results of subjective determination, presence or absence of strife/annoyance was labeled relative to a threshold value which was determined for each participant based on a method describe below. Hereinafter, these subjective determination labels will be treated as the participant states.

Figure 6:
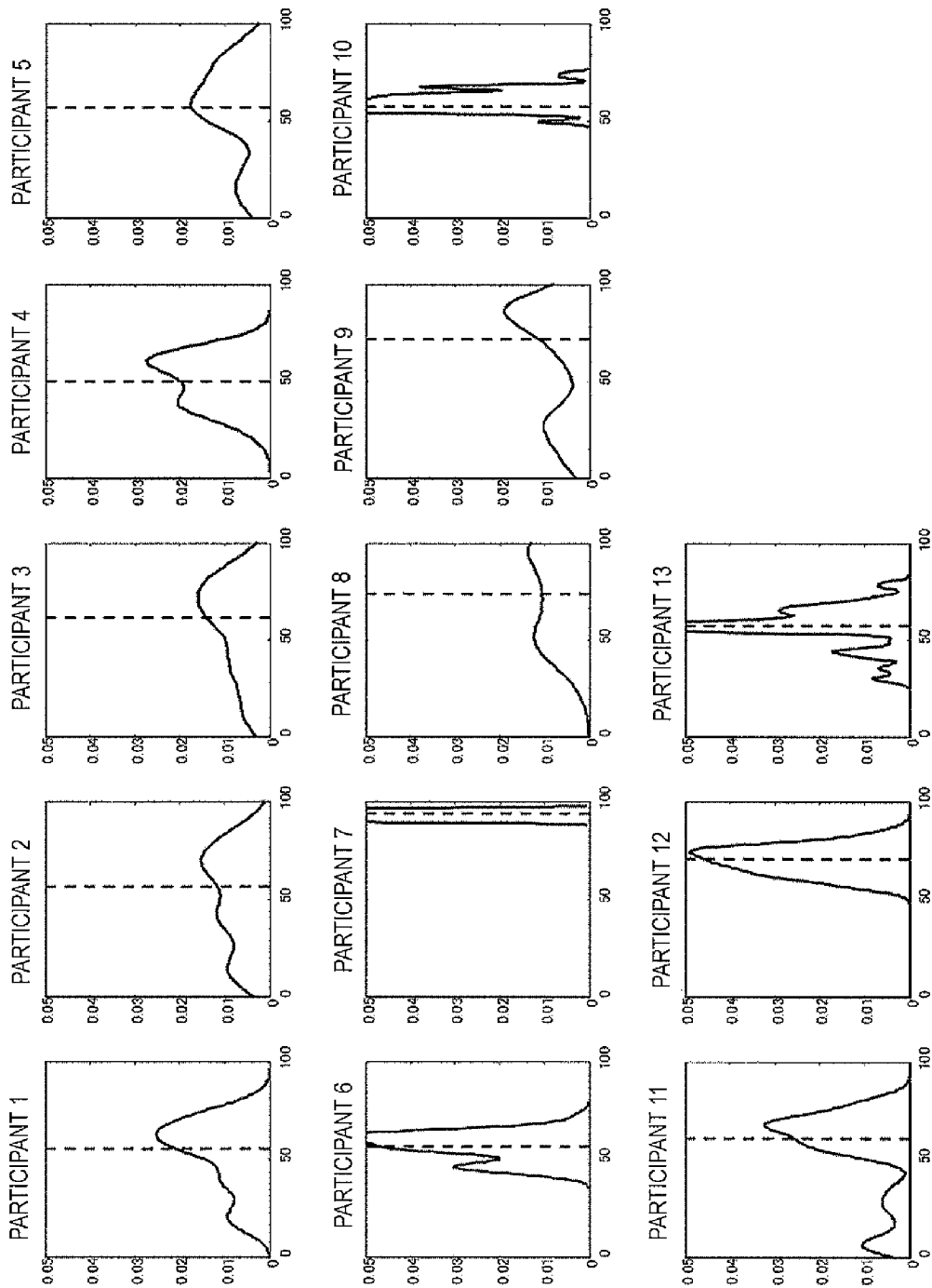
FIG. 6 is a diagram showing results of subjective determination of different participants concerning strife.

FIG. 6 shows results of subjective determination of different participants concerning strife. A proportion within all trials is shown each. Each solid line in FIG. 6 shows a distribution of results of subjective determination, whereas each broken line shows a threshold value at which subjective determinations (high strife/low strife) are split. Since subjective determination admits of large individual differences, the threshold value was determined based on the ordinal ranks of determination results (i.e., 1 to 100 on the visual analog scale) of each individual person. Specifically, a value which marks a median ordinal rank among the determination results of each individual person was defined as the threshold value. Herein, identical determination results were treated as pertaining to the same subjective determination (high strife/low strife).

FIG. 7 shows results of subjective determination of different participants concerning annoyance. A proportion within all trials is shown each. Each solid line in FIG. 7 shows a distribution of results of subjective determination, whereas each broken line shows a threshold value at which subjective determinations ("annoying"/"not annoying") are split. As in the case of strife, the inventors have determined the threshold value based on the ordinal ranks of determination results (i.e., 1 to 100 on the visual analog scale) of each individual person. Specifically, among the ordinal ranks of determination results of each individual person, the inventors have defined those determination results which account for a greater ⅓ as "annoying", and anything else as "not annoying", thus finding a threshold value. Herein, identical determination results were treated as pertaining to the same subjective determination ("annoying"/"not annoying").

Next, experimental results concerning strife will be described.

Hereinafter, event-related potential results will be described.

Figure 8A:
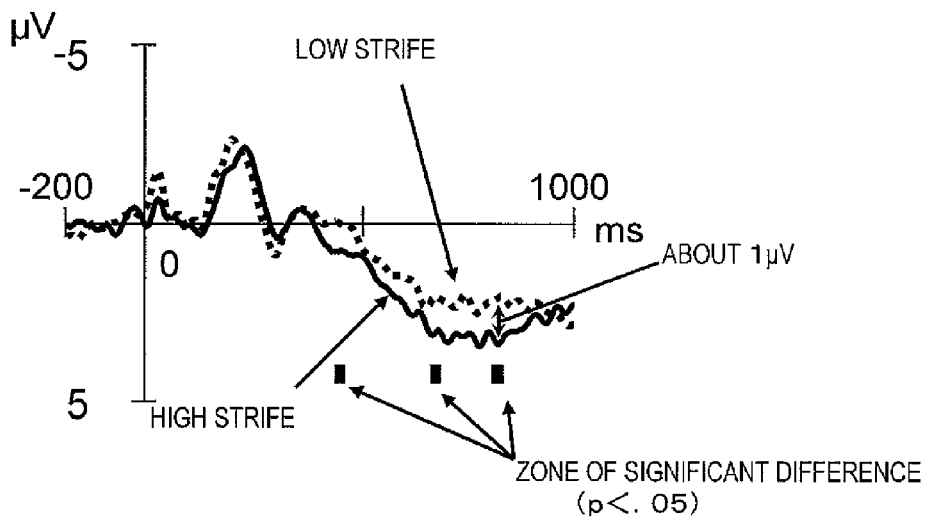
FIG. 8A is a waveform diagram obtained by taking a total arithmetic mean of event-related potentials at the parietal (Pz) based on audio presentation as a starting point, with respect to subjective determinations concerning strife.

First, results of taking an arithmetic mean based on the presence or absence of strife will be described. FIG. 8A shows waveforms obtained by taking a total arithmetic mean of event-related potentials at the parietal (Pz) based on audio presentation as a starting point, with respect to subjective determinations concerning strife. An arithmetic mean was taken based on the subjective determinations concerning strife for respective blocks, under the six conditions in the above-described measurement experiment. In FIG. 8A, the horizontal axis represents time in units of ms, whereas the vertical axis represents potential in units of μV. As is clear from the scales shown in FIG. 8A, the lower direction in the graph corresponds to plus (positive), and the upper direction corresponds to minus (negative). In FIG. 8A, a broken line represents a total arithmetic mean waveform in the case of determining low strife, and a solid line represents a total arithmetic mean waveform in the case of determining high strife.

Figure 8B:
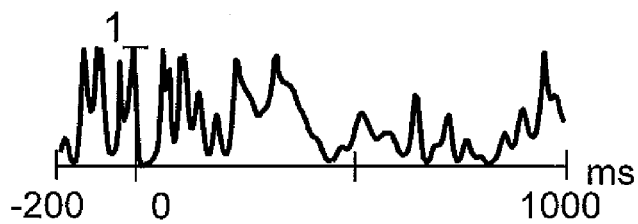
FIG. 8B is a diagram showing results of calculating p values for respective samplings.

It can be seen from FIG. 8A that positive components at a latency of 600 to 900 ms appear in the case of high strife (solid line), as compared to the case of low strife (broken line) in speech sound listening. The zone average potential from 600 to 900 ms for each subjective determination was: 1.99 μV in the case of low strife, and 2.73 μV in the case of high strife. As a result of t-testing the zone average potentials, there was a significant difference at the 10% level. FIG. 8B shows results of calculating p values at respective samplings. It can be seen from FIG. 8B that the p value is smaller in a time slot from about 600 to 900 ms, based on audio stimulation as a starting point, than in any other time slot. Therefore, there is a possibility that strife in speech sound listening is reflected in the positive potential at a latency of about 600 to 900 ms based on audio presentation as a starting point. A t-test conducted at every sampling between 0 ms and 1000 ms found the following time slots in which a significant difference due to a difference in subjective determination lasted for 15 ms or more: 420 to 445 ms; 655 to 670 ms; 730 to 745 ms; and 775 to 830 ms ($p<0.05$).

Next, experimental results concerning annoyance will be described.

First, results of taking an arithmetic mean based on the presence or absence of annoyance will be described.

Figure 9:
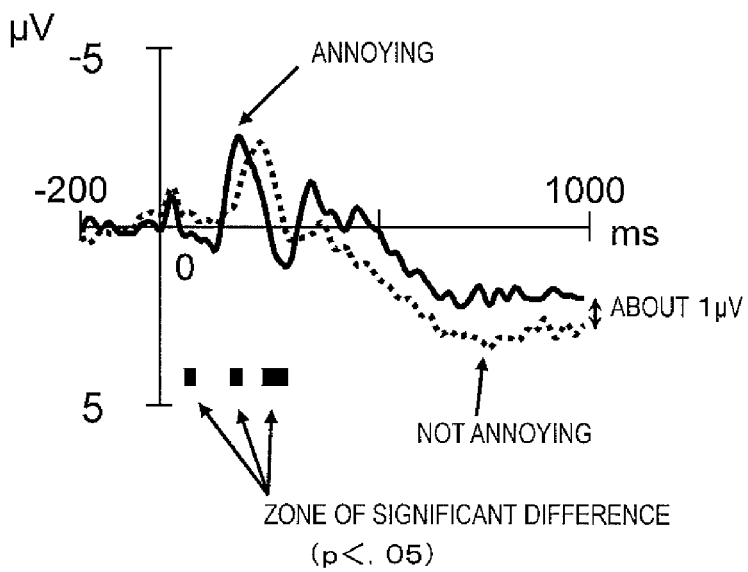
FIG. 9 is a waveform diagram obtained by taking a total arithmetic mean of event-related potentials at the parietal (Pz) based on audio stimulation as a starting point, with respect to subjective determinations concerning annoyance.

FIG. 9 shows waveforms obtained by taking a total arithmetic mean of event-related potentials at the parietal (Pz), based on audio stimulation as a starting point, with respect to subjective determinations concerning annoyance. An arithmetic mean was taken based on the subjective determinations concerning annoyance for respective blocks, under the six conditions in the above-described measurement experiment. In FIG. 9, the horizontal axis represents time in units of ms, whereas the vertical axis represents potential in units of μV. As is clear from the scales shown in FIG. 9, the lower direction in the graph corresponds to plus (positive), and the upper direction corresponds to minus (negative). In FIG. 9, a solid line represents a total arithmetic mean waveform in the case where the user found the audio to be "annoying" in the subjective determination, and a broken line represents a total arithmetic mean waveform in the case of where the user found the audio to be "not annoying" in the subjective determination.

It can be seen from FIG. 9 that a negative component (N1 component) which is induced at a latency of about 200 ms has a shorter latency in the case of "annoying" (solid line) than in the case of "not annoying" (broken line). The latency of the N1 component of each participant was 195 ms in the case of "annoying", and 240 ms in the case of "not annoying". As a result of t-testing the latencies, a significant difference was recognized ($p<0.05$). A zone average potential at a latency from 200 ms to 300 ms of each participant was 0.14 μV in the case of "annoying", and −1.38 μV in the case of "not annoying". As a result of t-testing the zone average potentials at latencies from 200 ms to 300 ms, the zone average potentials in the case of "annoying" were significantly larger ($p<0.05$).

Therefore, there is a possibility that the latency of an N1 component based on audio presentation as a starting point and an average potential of a negative component at about 200 to 300 ms based on audio presentation as a starting point reflect annoyance, and can be used as an index of annoyance in speech sound listening. A t-test conducted at every sampling between 0 ms and 1000 ms found the following time slots in which a significant difference due to a difference in subjective determination lasted for 15 ms or more: 50 to 70 ms; 155 to 175 ms; 225 to 290 ms; and 920 to 935 ms.

1.2. Electroencephalogram Measurement Experiment 2 (Experiment Concerning Speech Sound Intelligibility)

In Electroencephalogram measurement experiment 2, the inventors examined a relationship between speech sound intelligibility and the event-related potential after character presentation. Hereinafter, with reference to FIG. 10 to FIG. 13, the experimental setting and experimental results of Electroencephalogram measurement experiment 2 will be described.

Five undergraduate or graduate students with normal hearing participated in the experiment.

Each electroencephalogram was recorded from electrodes placed at the Fz, Cz, Pz, C3, and C4 (International 10-20 system) on the scalp as shown in FIG. 3A, on the basis of the right mastoid. The sampling frequency was 200 Hz, and the time constant was 1 second. It was subjected to a 0.1 to 6 Hz digital band-pass filter off-line. As an event-related potential in response to a character presentation, a waveform from −100 ms to 1000 ms was cut out based on the point of character presentation as a starting point. An arithmetic mean of event-related potentials was taken based on the results of button pressing acquired in electroencephalogram measurement experiment 3 (absolutely matching/absolutely mismatching).

Figure 10:
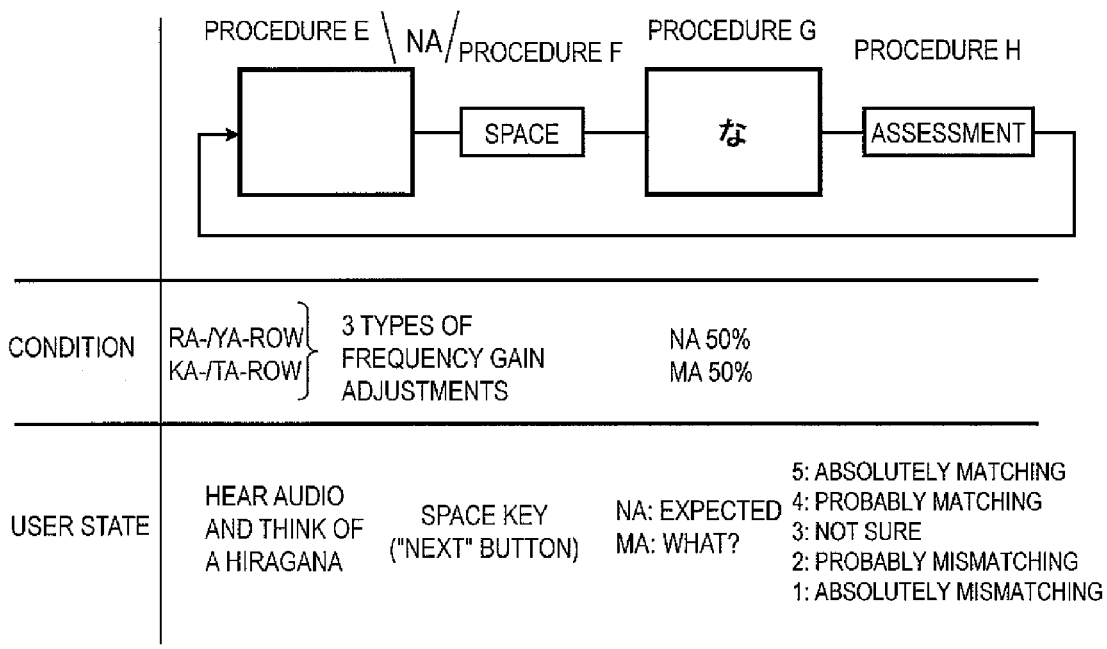
FIG. 10 is a diagram showing the experimental procedure in outline.

FIG. 10 is a diagram showing the experimental procedure in outline.

First, in Procedure E, monosyllabic audios were presented. The speech sounds are selected from among the na-row/ma-row, the ra-row/ya-row, and the ka-row/ta-row, which are supposed to induce mistakes in aural comprehension. Audios under the following three conditions featuring three different frequency gains were presented, thus resulting in varying ease of aural comprehension when listening to a speech sound.

(1) No gain adjustment condition: an audio to which no frequency gain adjustment has been applied is presented.
(2) Small gain condition: an audio whose gain at frequencies from 250 Hz to 16 kHz is gradually adjusted (reduced) to −25 dB is presented.
(3) Large gain condition: An audio whose gain at frequencies of 250 Hz to 16 kHz is gradually adjusted (reduced) to −50 dB is presented. In advance, the experimental participant was instructed to hear an audio and think of a corresponding character.

Figure 11:
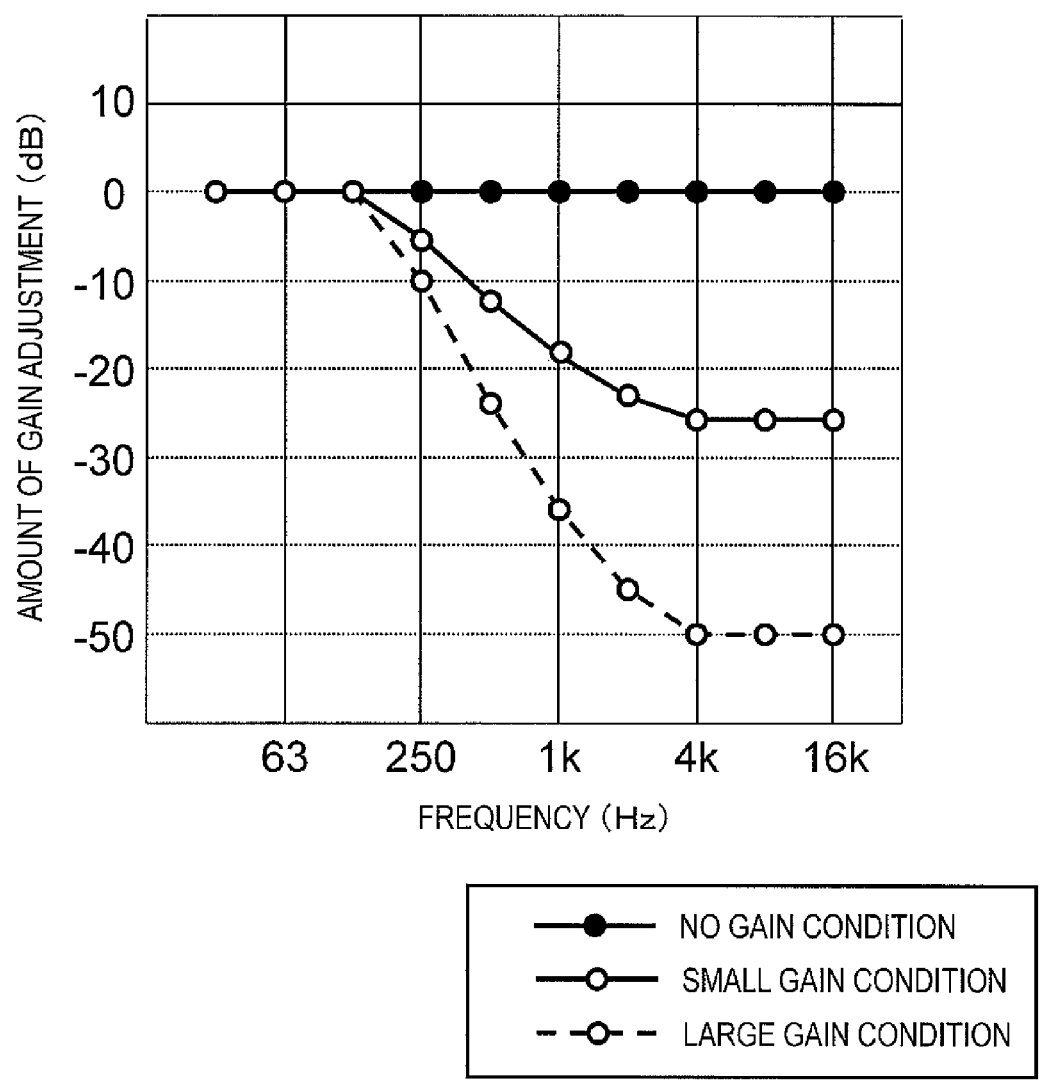
FIG. 11 is a diagram showing amounts of gain adjustment for different frequencies, respectively under conditions (1) to (3).

FIG. 11 shows amounts of gain adjustment for different frequencies under conditions (1) to (3). The reason why the frequency gain for the higher frequencies was decreased is in order to reproduce a typical pattern of hypacusia of elderly people, thus allowing people with normal hearing to experience a hearing which is similar to the difficult hearing of elderly people suffering from hypacusia.

Next, in Procedure F of FIG. 10, the experimental participant was asked to press the SPACE key on the keyboard. As the participant pressed the button, the procedure would proceed to the next Procedure G. This Procedure F was introduced in order to allow the participant to experience the character stimulation of Procedure G at his or her own pace.

In Procedure G, a character was presented on a display. With a probability of 50%, characters not matching the audio presented in Procedure E were presented so that a participant with normal hearing would feel mismatchingness. As each mismatching character, a character in a different row from that of the audio was chosen, from within a pair of na- and ma-rows, a pair of ra- and ya-rows, or a pair of ka- and ta-rows, which are supposed to induce mistakes in aural comprehension, while the vowel was not changed. For example, if "な (na)" was presented in procedure E, then "た" was to be presented as a matching condition in procedure G, and "ま (ma)" was to be presented as a mismatching condition. In this case, if the participant aurally comprehended the audio correctly, then he or she would feel expectedness in response to "な (na)" being presented, and unexpectedness in response to "ま (ma)" being presented.

Procedure H was provided for confirming how mismatching the audio presented in Procedure E and the character presented in Procedure G were to the participant. The participant was supposed to press the number "5" on the keyboard to express "absolutely matching", "4" to express "probably matching", "3" to express "not sure", "2" to express "probably mismatching", and "1" to express "absolutely mismatching".

The inventors carried out the experiment so that Procedure E to Procedure H to was repeated 108 times (108 trials). In this experiment, three sounds in the ma•na/ya•ra/ka•ta-rows were used as speech sounds for presentation, these speech sounds having been subjected to three levels of gain adjustment (totaling 54 audios).

Figure 12:
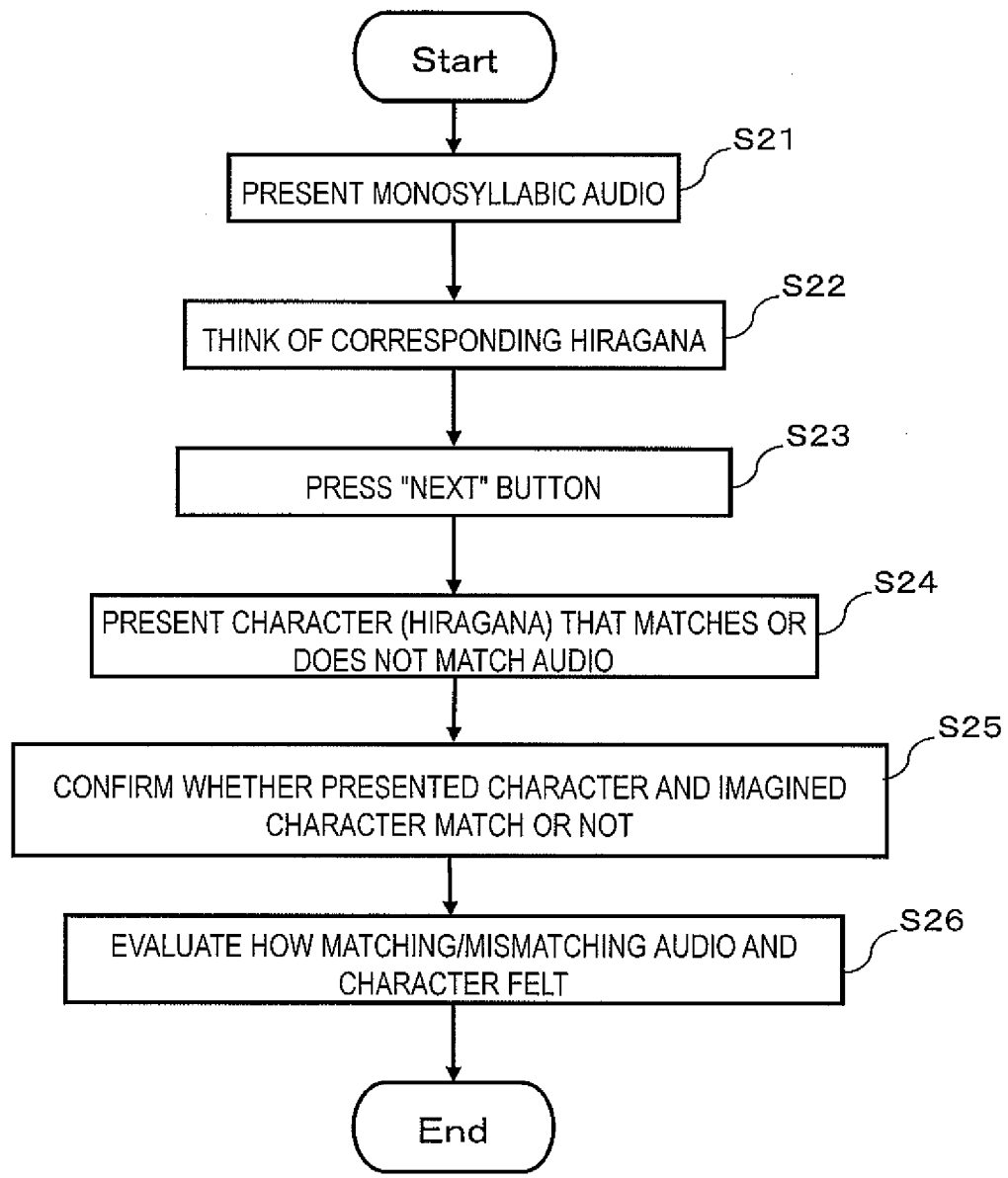
FIG. 12 is a flowchart showing a procedure corresponding to one trial.

FIG. 12 is a flowchart showing a procedure corresponding to one trial. In this flowchart, for ease of explanation, the operation of the apparatus and the operation of the experimental participant are both present.

At step S21, a monosyllabic audio is presented to the experimental participant.

At step S22, the participant hears the monosyllabic audio and thinks of a corresponding character.

At step S23, the participant presses the SPACE key as a "NEXT" button.

Step S24 is a step of presenting on a display a character matching the audio or a character mismatching the audio, based on step S23 as the starting point. The probability that the audio and the character would match was 50%; therefore, the probability that the audio and the character would be mismatching was also 50%.

At step S25, the participant confirms whether the character which the participant thought of at step S22 matched the character presented at step S24.

At step S26, the participant answers how matching/mismatching they were felt to be at step S25, via number keys of 1 to 5.

Figure 13:
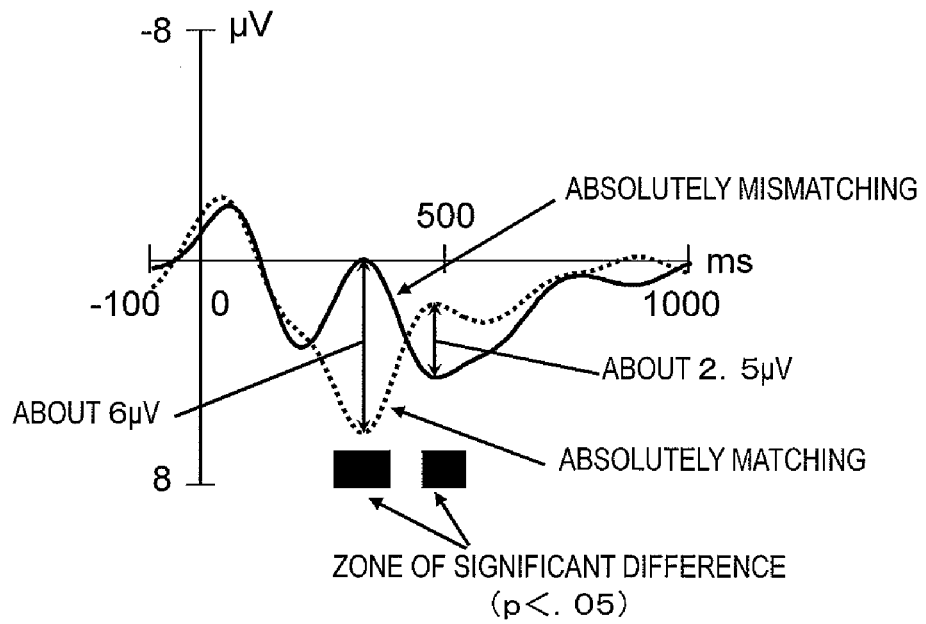
FIG. 13 is a diagram showing results obtained by taking a total arithmetic means of event-related potentials at the parietal electrode position (Pz), with respect to subjective determinations as to absolutely mismatching/absolutely matching.

FIG. 13 shows results obtained by taking a total arithmetic means of event-related potentials at the parietal electrode position (Pz), with respect to subjective determinations as to absolutely mismatching/absolutely matching. As each stimulation, an event-related potential from −100 to 1000 ms based on the point of character presentation as 0 ms is used for the calculation. In FIG. 13, the horizontal axis represents time in units of ms, whereas the vertical axis represents potential in units of μV. In the graph, the lower direction corresponds to plus (positive), and the upper direction corresponds to minus (negative). A baseline correction was performed so that an average potential from −100 ms 0 ms would be 0.

The solid line shown in FIG. 13 represents an arithmetic mean waveform of the event-related potential in the case where the participant feels mismatchingness, whereas the broken line represents an arithmetic mean waveform of the event-related potential in the case where the participant feels matchingness. It can be seen from FIG. 13 that: (1) as compared to the solid line where the participant felt mismatchingness, the broken line where the participant felt matchingness exhibited a positive component in the range around a latency from 200 ms to 400 ms; and (2) as compared to the broken line where the participant felt matchingness, the solid line where the participant felt mismatchingness exhibited a positive component in the range around a latency from 500 ms to 600 ms. As a result of performing a t-test for every sampling from 0 ms to 1000 ms, it was found that the time slots where a significant difference ($p<0.05$) due to the aforementioned difference in speech sound intelligibility lasted for 20 ms or more were 270 ms-390 ms and 450 ms-540 ms.

From these results of the electroencephalogram measurement experimentation, it was found that determinations of (1) strife, (2) annoyance, and (3) speech sound intelligibility can be made by checking for event-related potential components at specific latencies.

Next, the relationship between the distinction ratio and the number of summations will be described.

The inventors conducted an analysis of electroencephalogram data for identifying a number of summations required for each of the components found through the above experimentation to be used in the determination. With respect to each of the three particular event-related potentials for making the respective determinations, the distinction ratio was studied by sequentially increasing the number of summations, which indicated that, when a certain distinction ratio (e.g., 80%) is to be achieved: (1) the required number of summations greatly varies from item to item of determination; (2) the speech sound intelligibility determination requires a smaller number of summations than the number of summations (i.e., 20 times) that is conventionally considered necessary for electroencephalogram measurement; and (3) the comfortableness determination requires an even greater number of summations than the number of summations (i.e., 20 times) that is conventionally considered necessary for electroencephalogram measurement.

Hereinafter, the details of an analysis which was conducted with respect to the three items of determination (strife, annoyance, and speech sound intelligibility) will be described.

As for strife, a distinction between "high strife/low strife" subjective reports was made by using an event-related potential measured in Electroencephalogram measurement experiment 1.

First, as many waveforms as the number of summations were randomly chosen from among the waveforms for all trials under each of the "high strife/low strife" conditions, and an arithmetic mean thereof was taken. The inventors obtained 20 such arithmetic mean waveforms for each condition.

Next, from each arithmetic mean waveform, an average potential in the zone (600 ms to 900 ms) which was found to produce a significant difference in the aforementioned experiment was calculated, and this average potential was defined as the characteristic amount. Moreover, for a total arithmetic mean waveform under each of the "high strife/low strife" conditions, an average potential in this same zone was also calculated, and an average value therebetween was defined as the threshold value. Then, if a calculated result of the characteristic amount was greater than the threshold value, "high strife" was determined; if smaller, "low strife" was determined. The rate of correct results of distinction, against all waveforms, was defined as the distinction ratio.

As for annoyance, a distinction between "annoying/not annoying" subjective reports was made by using the event-related potential measured in Electroencephalogram measurement experiment 1. First, as many waveforms as the number of summations were randomly chosen from among the waveforms for all trials under each of the "annoying/not annoying" conditions, and an arithmetic mean thereof was taken. The inventors obtained 20 such arithmetic mean waveforms for each condition.

Next, from each arithmetic mean waveform, an average potential and an N1 latency in the zone (200 ms to 300 ms) which was found to produce a significant difference in the aforementioned experiment were calculated, and these were defined as the characteristic amounts (two-dimensional).

Now, a border of distinction for distinguishing between "annoying/not annoying" with respect to these characteristic amounts is described. The border-of-distinction calculation employed total arithmetic mean waveforms. For each of the "annoying/not annoying" conditions, an average potential and N1 latency of a total arithmetic mean waveform were calculated in the same zone as that used in obtaining the characteristic amount. The average potential and N1 latency calculated under each of the "annoying/not annoying" conditions is plottable as a "point" in a potential-time graph. Regarding a straight line connecting these two points, a perpendicular extending through a midpoint of this straight line was defined as the border of distinction. Then, if a calculated result of the characteristic amount was located above the border of distinction, it was distinguished as "annoying"; if below, "not annoying". The rate of correct results of distinction, against all waveforms, was defined as the distinction ratio.

Next, a determination process of speech sound intelligibility will be described.

As for speech sound intelligibility, a distinction between "absolutely matching/absolutely mismatching" subjective reports was made by using an event-related potential measured in Electroencephalogram measurement experiment 2. First, as many waveforms as the number of summations were randomly chosen from among the waveforms for all trials under each of the "absolutely matching/absolutely mismatching" conditions, and an arithmetic mean thereof was taken. For each condition, 20 such arithmetic mean waveforms were obtained. Next, from each arithmetic mean waveform, an average potential in a zone (270 ms to 390 ms, 450 ms to 540 ms) which was found to produce a significant difference in the aforementioned experiment was calculated, and a difference therebetween was defined as the characteristic amount. Moreover, for a total arithmetic mean waveform under each of the "absolutely matching/absolutely mismatching" conditions, an average potential difference in this same zone was also calculated, and an average value therebetween was defined as the threshold value. By using this threshold value, a distinction was made such that: if a calculated result of the characteristic amount was greater than the threshold value, it was distinguished as "absolutely matching", and if small, "absolutely mismatching". The rate of correct results of distinction, against all waveforms, was defined as the distinction ratio.

Figure 14:
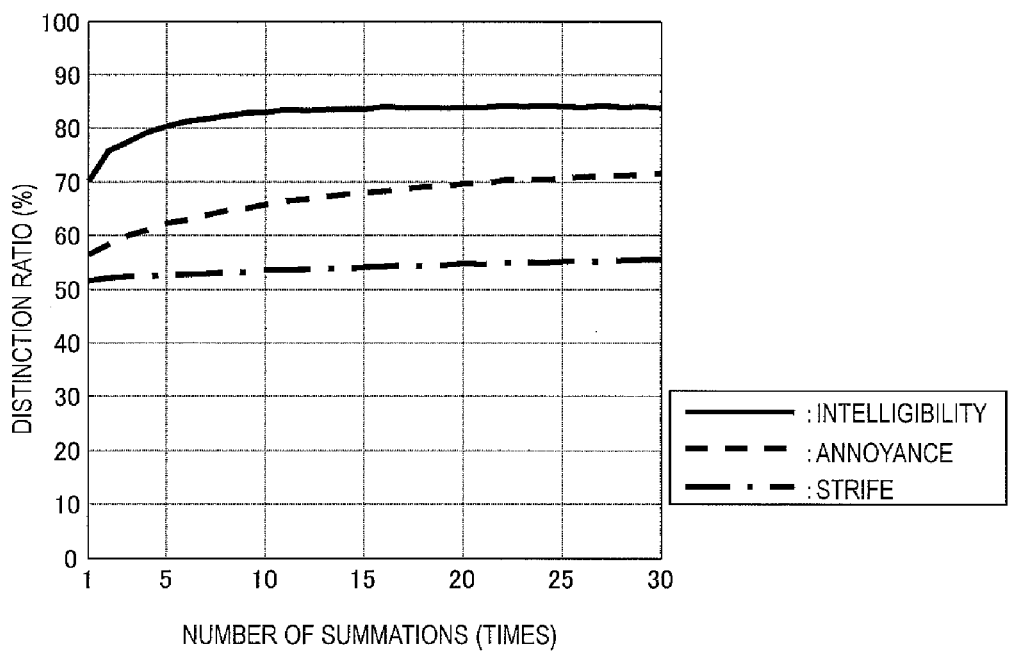
FIG. 14 is a diagram showing changes in the distinction ratio with respect to three items of determination, where the number of summations is varied.

From the experiments, the inventors were able to obtain the following data concerning the relationship between the number of summations and the distinction ratio. FIG. 14 shows changes in the distinction ratio when the number of summations is varied, regarding the above three items of determination. The distinction ratio in FIG. 14 represents average values when the aforementioned calculation is repeated 100 times. It can be seen from FIG. 14 that, despite some fluctuation caused by the small number of test subjects, basically in all items of determination, the distinction ratio improves as the number of summations (horizontal axis) increases. However, it can also be said that the distinction ratio for strife is unlikely to increase even if the number of summations is increased.

On the other hand, regarding the distinction ratio of each item of determination, it is apparent that there exist different relationships between the number of summations and the distinction ratio, depending on the item of determination. Although the distinction accuracy for speech sound intelligibility reaches 80% at 5 summations, the distinction accuracy for annoyance reaches 70% at 20 summations. Furthermore, even at greater numbers of summations, the distinction accuracy for strife falls short of the distinction accuracies for speech sound intelligibility and annoyance. Such are the characteristics which the inventors have found through their experimentation.

The reason why these characteristics are observed may be the different magnitudes of the respective electroencephalogram components.

The potential differences in the zones which are used for the distinction of speech sound intelligibility as shown in FIG. 13 (the potential differences indicated as "about 6 µV" and "about 2.5 µV" in FIG. 13) greatly differ from the potential difference in the zone which is used for distinguishing comfortableness as shown in FIG. 8 and FIG. 9 (the potential difference indicated as "about 1 µV" in each figure).

There may be two reasons for this. A first reason may be the different stimulation types. Since determination of speech sound intelligibility is based on reactions to visual stimulations, generally greater reactions than reactions to auditory stimulations are likely to occur, thereby resulting in large electroencephalogram components. On the other hand, comfortableness ("strife" and "annoyance") is reactions to auditory stimulations, so that the electroencephalogram component is considered to become smaller in magnitude than in reactions to visual stimulations.

A second reason may be the different substances of determination. Speech sound intelligibility permits clear determination based on whether a speech sound as aurally distinguished matches a presented character. On the other hand, comfortableness consists in ambiguous determination as to whether something is comfortable or not. Therefore, it is believed that the electroencephalogram component will be greater in speech sound intelligibility determination than in comfortableness determination. Thus, although possibly the distinction accuracies that were obtained through the present experiment might have increased or decreased depending on the method of identification or the like, it is still believed that the ordinal relationship between the distinction accuracies of speech sound intelligibility and comfortableness would not have changed, because of the different stimulation types and electroencephalogram components.

Now, the required number of summations for each item of determination will be discussed. A required number of summations is determined from a relationship between the number of summations and the distinction ratio. For example, if a 80% distinction accuracy is needed in speech sound intelligibility determination, then the required number of summations will be 5. Thus, a required number of summations is to be determined from the required distinction accuracy for each item of determination. Therefore, it is expected that the required number of summations will vary as the distinction accuracy changes, and will also vary depending on the substance of the hearing determination to be conducted, because of the possibility for the required accuracy to change. Hereinafter, in order to describe the required number of summations, it is assumed that the accuracy required of speech sound intelligibility determination is 80%, and the accuracy required of comfortableness determination is 70%, this being only an example.

The above can be summarized as follows, as shown in FIG. 14: to achieve a certain distinction ratio (a 80% speech sound intelligibility or a 70% comfortableness in this case), a smaller number of summations than the conventionally-required number of summations (i.e., 20 times) is needed for intelligibility, but a number of summations which is equal to or greater than the conventional number of summations is needed for comfortableness. However, although intelligibility and comfortableness require different numbers of summations, these are to be determined as reactions to a sequence of audio presentation and character presentation; therefore, it is only single reactions of intelligibility and comfortableness that are obtained through one trial.

In order to maintain a distinction accuracy for comfortableness, it is necessary that the number of summations is equal to or greater than the conventional 20 times. However, increasing the number of summations will result in a long presentation time. For example, if the 20 speech sounds of the 67S list are used for determining speech sound intelligibility, twenty presentations of 20 speech sounds will result in a total of 400 presentations. This means that the test subject must concentrate on the aurally distinction of audios throughout the 400 presentations, which will be a large burden on the test subject. Moreover, the time required for the selection is estimated as follows: assuming three levels of sound pressure of the presented audio, and 3 seconds of interval between audio stimulations, it will take at least 2 hours for 400 presentations if hearing determinations are to be made when a hearing aid is not worn and when a hearing aid is worn.

Regarding the relationship between the number of summations and the presentation time, the inventors have paid attention to the different required numbers of summations for speech sound intelligibility and comfortableness, and to the different resolutions that are required for speech sound intelligibility and comfortableness determinations.

As used in the present specification, a "resolution" of determination is a notion indicating whether an output determination result to be finally utilized is each individual speech sound or several speech sounds in a batch. As for the speech sound intelligibility determination, in order to determine whether a speech sound has been aurally distinguished or not, it is necessary to make a correct/incorrect determination for each speech sound. As for the annoyance and strife determinations in comfortableness determinations, however, there is no need to make a comfortable/uncomfortable determination for each speech sound, but those speech sounds which are heard in similar manners under the same condition (e.g., the same sound pressure) may be subjected to a batch determination. It can be said that this concept has been unprecedentedly arrived at by the inventors as a result of analyzing user hearing when making comfortableness determinations. Hereinafter, it will be described in detail.

First, regarding a user's hearing when making comfortableness determinations, strife determination and annoyance determination will be respectively described. As has been described earlier, strife is an index of how much strife a user has made in aurally distinguishing a speech sound. In a situation where a user cannot aurally distinguish speech sounds, it is presumable that an inability to distinguish exists because the speech sounds are close in frequency, rather than in the sound pressure level of presentation. Therefore, it is considered that a batch determination of strife can be made on a frequency basis.

Figure 15:
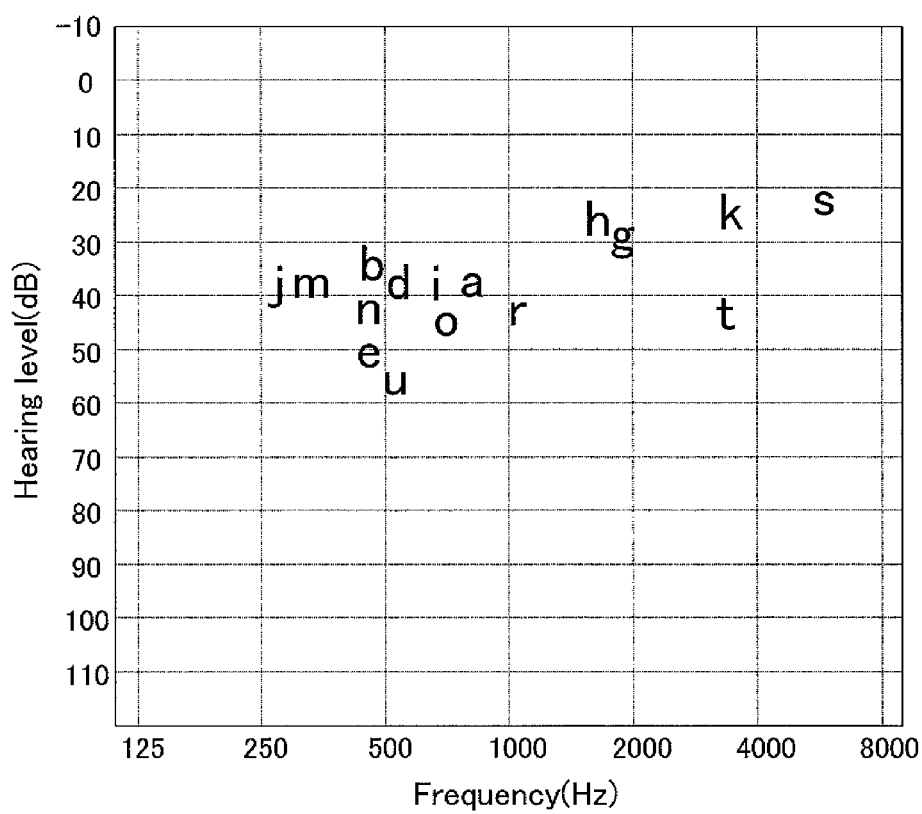
FIG. 15 is a diagram in which hearing levels of different phonemes are plotted against frequency.

FIG. 15 is a diagram in which hearing levels of different phonemes are plotted against frequency. It can be seen from FIG. 15 that the phoneme distribution is deviated (frequency deviation). Therefore, when determining strife in a batch, grouping may be made based on each cluster in the distribution of FIG. 15, or any huddle of speech sounds.

Figure 16:
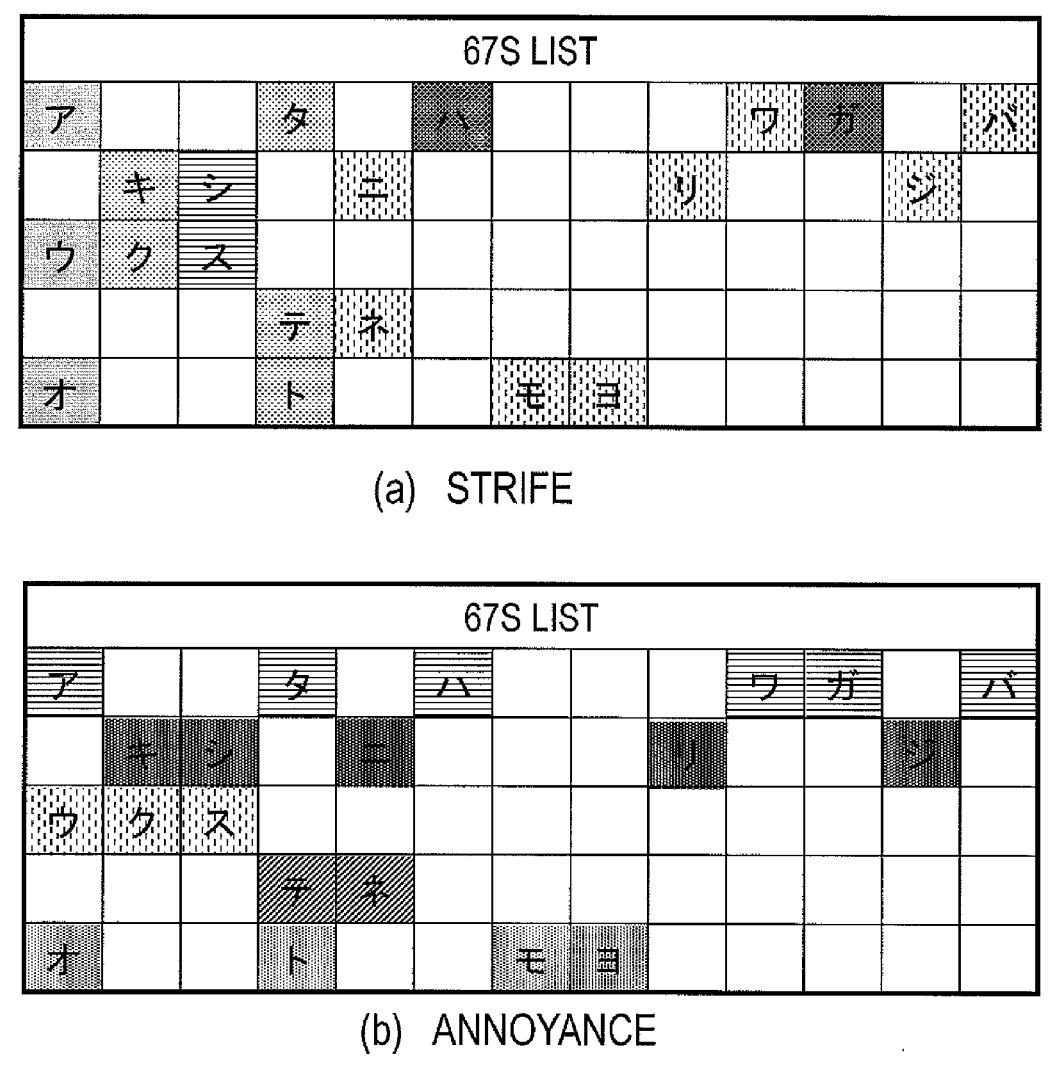

On the other hand, annoyance is hardly affected by the different frequency bands of sounds, but a direct factor thereof is the amplitude levels of sounds. Therefore, it is considered that grouping can be made based on the vowel type, which is a determiner of the amplitude level of a speech sound. As mentioned earlier, a batch determination for audios of the same sound amplitude or the same frequency band will not be much different from a comfortableness determination which is made for each individual speech sound. In other words, speech sound intelligibility determination can be said to require a finer-resolution determination. FIG. 16 shows an exemplary grouping of the 20 speech sounds in the 67S list which is made according to the above. Specifically, FIG. 16(a) shows an exemplary grouping of the 20 speech sounds in the 67S list with respect to strife, which is made according to the distribution in FIG. 15.

For example, "シ (shi)" and "ス (su)" in FIG. 16(a) are categorized in an "s" group that is located near a frequency of about 6000 Hz in FIG. 15. Moreover, "キ (ki)", "ク (ku)", "タ (ta)", "テ (te)", and "ト (to)" in FIG. 16(a) are categorized in a "k" and "t" group that is located near a frequency of about 3500 Hz in FIG. 15. Furthermore, "ハ (ha)" and "ガ (ga)" in FIG. 16(a) are categorized in an "h" and "g" group that is located near a frequency of about 1800 Hz in FIG. 15.

On the other hand, FIG. 16(b) shows an exemplary grouping of the 20 speech sounds in the 67S list with respect to annoyance, which is made for each vowel.

Figures 17, 18:
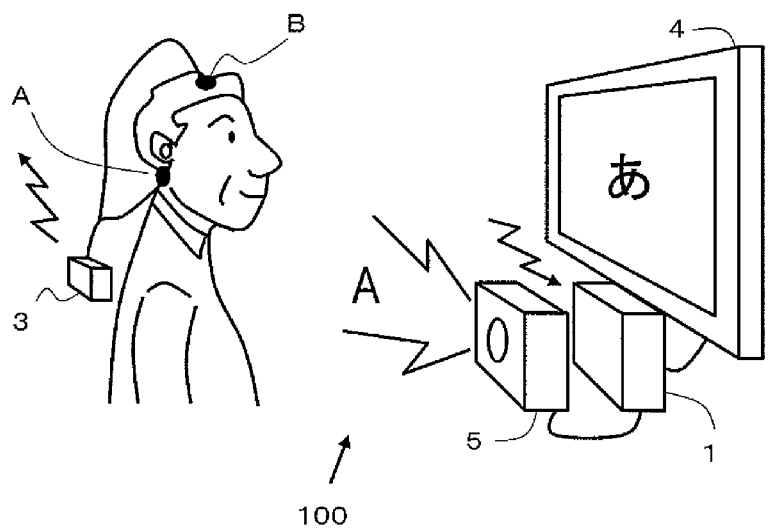
FIG. 17 is a diagram showing relationship between determination methods, as compiled by the inventors.
FIG. 18 is a diagram showing a construction and an environment of use for a hearing determination system 100 of Embodiment 1.

From these, and in universally considering the required resolution of determination and the required number of summations, the inventors have found that the number of summations may be small for intelligibility determination, which requires a fine-resolution determination, whereas a batch determination across a plurality of speech sounds can be made for comfortableness determination, which requires a large number of summations. FIG. 17 is a diagram showing relationship between determination methods, as compiled by the inventors.

From this finding, the inventors have arrived at the concept that, regarding items of hearing determination that require different numbers of summations, the total number of audio and character presentations can be reduced by selectively using different portions of the electroencephalogram for arithmetic mean depending on the item of determination.

Hereinafter, the details of embodiments of the present disclosure accomplished based on the above concept, as well as effects thereof, will be described by referring to the drawings, with reference to an exemplary case where annoyance determination is performed as a comfortableness determination.

In the present specification, in order to define a component of an event-related potential, a point in time after the lapse of a predetermined time since a given point is expressed by referring to a "latency of about 750 ms", for example. This means possible inclusion of a range around the specific point of 750 ms in time. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI— (or "Event-Related Potential (ERP) Manual—mainly concerning P300—"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 300 ms±30 ms, 750 ms±50 ms).

Although the aforementioned "breadth of 30 ms to 50 ms" is a generic example of an individual difference in the P300 component, greater individual differences exist between users with respect to the aforementioned positive component at a latency of about 750 ms, which is later in latency than P300. Therefore, the aforementioned positive component is preferably treated as having a broader breadth, e.g., a breadth of about 100 ms to 150 ms on each of the earlier side and the later side. Accordingly, in the present embodiment, a "latency of about 750 ms" is meant to indicate a latency from 600 ms to 900 ms. A latency from 600 ms to 900 ms means a latency of no less than 600 m and no more than 900 ms.

Similarly, "near a latency of 200 ms" and "a latency of about 200 ms" may be construed as having a breadth of 30 ms to 50 ms on each of the earlier side and the later side of the latency of 200 ms, or even having a slightly greater breadth, e.g., a breadth of 50 ms to 100 ms on each of the earlier side and the later side. In other words, in the present embodiment, a "latency of about 200 ms" may be construed as a latency of no less than 100 ms and no more than 300 ms.

Note that a "positive component" would generally mean a potential which is greater than 0 μV. However, in the context of the present specification, it is not a requirement for a "positive component" to be absolutely positive (i.e., greater than 0 μV). In the present specification, the presence or absence of a "positive component" is identified in order to distinguish a high or low confidence of aural distinction; so long as a significant highness or lowness of confidence of aural distinction is distinguishable, it does not matter if the zone average potential, etc., is 0 μV or less.

Note that a "negative component" would generally mean a potential which is smaller than 0 μV. However, in the context of the present specification, it is not a requirement for a "negative component" to be absolutely negative (i.e., smaller than 0 μV). In the present specification, the presence or absence of a "negative component" is identified in order to distinguish whether annoyingness is felt; so long as annoyingness is distinguishable, it does not matter if the zone average potential, etc., is 0 μV or more. Whenever the relative largeness and smallness of a negative component is distinguishable, it is described in terms of "presence or absence" of the negative component.

2. Embodiment 1

FIG. 18 shows a construction and an environment of use for a hearing determination system 100 according to the present embodiment.

The hearing determination system 100 includes a hearing determination apparatus 1, a biological signal measurement section 3, a visual stimulation presentation section 4, and an auditory stimulation presentation section 5. The biological signal measurement section 3 is connected to at least two electrodes A and B. For example, electrode A is attached at a mastoid of a user 5, whereas electrode B is attached at a position (so-called Pz) on the scalp of the user 5.

The hearing determination system 100 presents monosyllabic speech sound to the user 2, in the form of an audio and then as a character. Based on an electroencephalogram (event-related potential) of the user 2 which is measured based on the point of audio presentation as a starting point, a comfortableness determination is made. Moreover, based on an electroencephalogram (event-related potential) of the user 2 which is measured based on the point of character presentation as a starting point, a speech sound intelligibility determination is made.

An electroencephalogram from the user 2 corresponding to a potential difference between electrode A and electrode B is acquired by the biological signal measurement section 3. The biological signal measurement section 3 sends information corresponding to the potential difference (electroencephalogram signal) to the hearing determination apparatus 1 in a wireless or wired manner. FIG. 18 illustrates an example where the biological signal measurement section 3 wirelessly sends the information to the hearing determination apparatus 1.

The hearing determination apparatus 1 performs sound pressure control of the audio used for hearing determination, controls presentation timing of the audio and the character, and presents to the user 2 an audio via the auditory stimulation presentation section 5 (e.g., loudspeakers) and a character via the visual stimulation presentation section 4 (e.g., a display).

Figure 19:
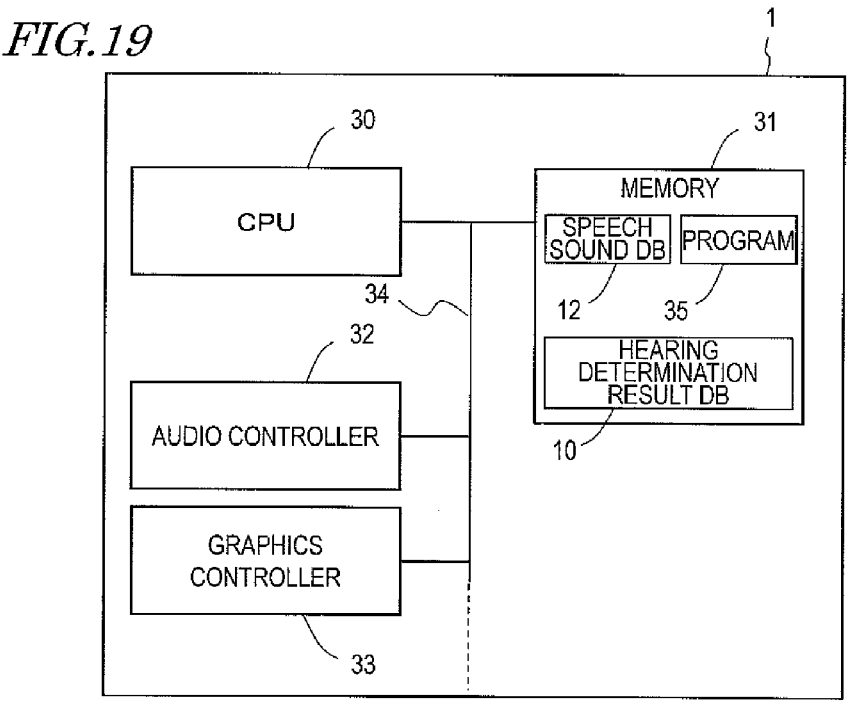
FIG. 19 is a diagram showing the hardware construction of a hearing determination apparatus 1 according to Embodiment 1.

FIG. 19 shows a hardware construction of the hearing determination apparatus 1 according to the present embodiment. The hearing determination apparatus 1 includes a CPU 30, a memory 31, an audio controller 32, and a graphics controller 33. These elements are interconnected via a bus 34, so that data exchange among them is possible.

The CPU 30 executes a computer program 35 which is stored in the memory 31. A processing procedure as illustrated by a subsequently-described flowchart is described in the computer program 35. In accordance with the computer program 35, the hearing determination apparatus 1 performs a process of controlling the entire hearing determination system 100, by utilizing a speech sound DB 12 which is also stored in the same memory 31. Moreover, the determination results by the hearing determination apparatus 1 are stored to a hearing determination result DB 10 within the memory 31. This process will be described in detail later.

In accordance with instructions from the CPU 30, the audio controller 32 generates an audio to be presented, and outputs the generated audio signal to the auditory stimulation presentation section 5 at a designated sound pressure.

In accordance with instructions from the CPU 30, the graphics controller 33 generates a character to be presented, and outputs it to the visual stimulation presentation section 4.

The respective functional blocks (excluding the speech sound DB 12) of the hearing determination apparatus 1, described later, correspond to functions which are occasionally realized by the CPU 30, the memory 31, the audio controller 32, and the graphics controller 33 as a whole when the program 35 shown in FIG. 19 is executed.

Figure 20:
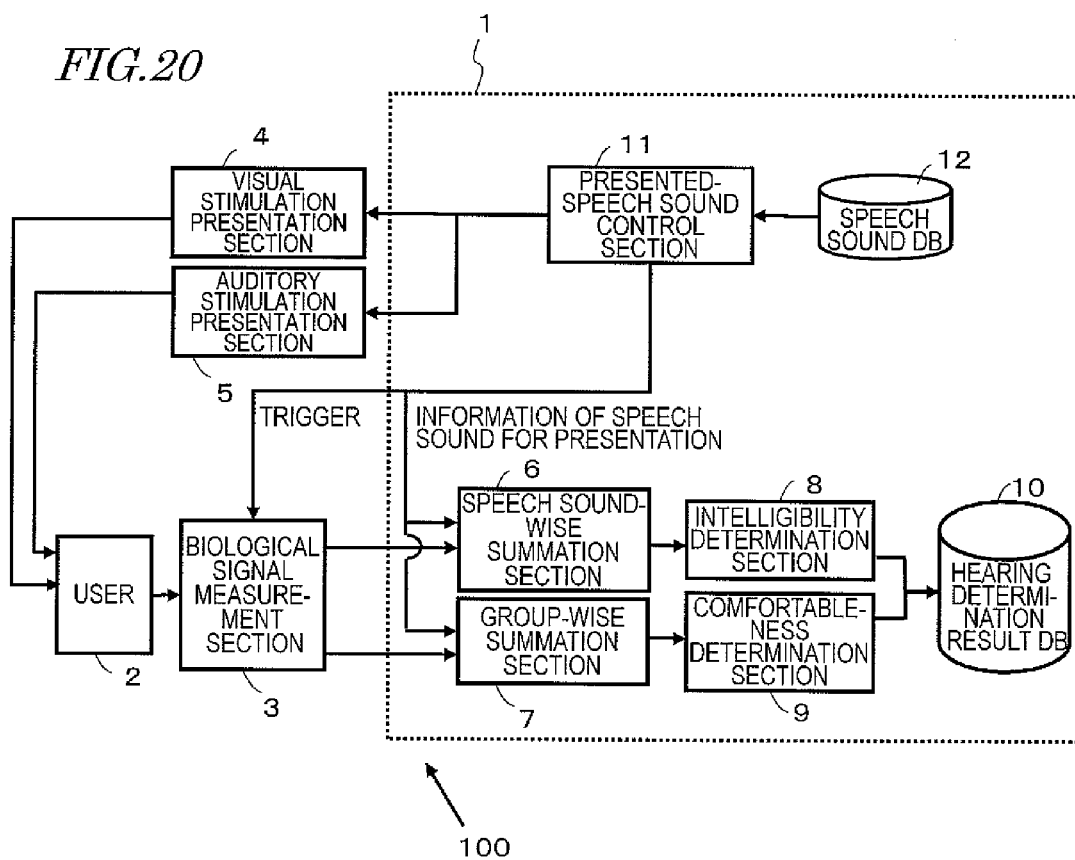
FIG. 20 is a block configuration diagram of the hearing determination system 100 of Embodiment 1.

FIG. 20 shows a block configuration diagram of the hearing determination system 100 according to the present embodiment.

The hearing determination system 100 includes the hearing determination apparatus 1, the biological signal measurement section 3, the visual stimulation presentation section 4, and the auditory stimulation presentation section 5. The user 2 block is illustrated for ease of explanation.

The hearing determination system 100 is employed when making a hearing determination by utilizing an electroencephalogram signal of the user 2. Hearing determination is performed by the hearing determination apparatus 1.

Hereinafter, functions of the component elements of the hearing determination system 100 will be described in outline. The detailed functions and constructions will be described in detail later.

The biological signal measurement section 3 measures an electroencephalogram of the user, and extracts event-related potentials based on audio and character stimulations respectively as starting points. In accordance with an instruction from the hearing determination apparatus 1, the visual stimulation presentation section 4 presents a character representing a speech sound to the user. The presented character serves as a stimulation to the visual sense of the user 2. In accordance with an instruction from the hearing determination apparatus 1, the auditory stimulation presentation section 5 presents an audio of a speech sound to the user. The presented audio serves as a stimulation to the auditory sense of the user 2.

The hearing determination apparatus 1 includes a speech sound-wise summation section 6, a group-wise summation section 7, an intelligibility determination section 8, a comfortableness determination section 9, the hearing determination result database (DB) 10, a presented-speech sound control section 11, and the speech sound database (DB) 12.

By utilizing data of a group(s) of a plurality of speech sounds, the group-wise summation section 7 takes a group-by-group summation of event-related potentials based on audio presentation as starting points. At least one such group may exist. Each group is categorized according to predetermined rules, e.g., a vowel group, an unvoiced consonant group, and a voiced consonant group. However, depending on the rules, there may be a group(s) having no member speech sounds.

From the electroencephalogram waveform which has been added up in a speech sound-by-speech sound manner, the intelligibility determination section 8 determines a speech sound intelligibility for each speech sound.

From the electroencephalogram waveform which has been added up in a group-by-group manner, the comfortableness determination section 9 determines a comfortableness for each group.

The hearing determination result DB 10 stores the determination results.

By referring to the speech sounds therein, the presented-speech sound control section 11 determines a speech sound to be presented to the user.

By utilizing the speech sound information, the speech sound-wise summation section 6 takes a speech sound-by-speech sound summation of event-related potentials based on character stimulation presentation as starting points.

The speech sound DB 12 stores speech sounds and grouped data of speech sounds.

Hereinafter, the respective blocks will be described in detail.

The biological signal measurement section 3 is a device for measuring potential changes in electrodes which are worn on the head of the user 2, and may be an electroencephalograph, for example. For example, a probe electrode is placed at the parietal (Pz), and a reference electrode is placed at the right or left mastoid, whereby an electroencephalogram as a potential difference between the probe electrode and the reference electrode is measured. The biological signal measurement section 3 measures an electroencephalogram of the user 2, and cuts out an event-related potential in a predetermined zone (e.g., a zone from −200 ms to 1000 ms) based on a trigger which is received from the presented-speech sound control section 11 as a starting point. At this time, any event-related potential that is based on a trigger corresponding to an auditory stimulation as starting point is sent to the group-wise summation section 7, and any event-related potential that is based on a trigger corresponding to a visual stimulation as a starting point is sent to the speech sound-wise summation section 6.

The present embodiment illustrates that the biological signal measurement section 3 cuts out an event-related potential in a predetermined range based on a trigger from the presented-speech sound control section 11 as a starting point, subjects it to a baseline correction, and sends the potential waveform data to the speech sound-wise summation section 6 or the group-wise summation section 7. However, this process is exemplary. In another process, for example, the biological signal measurement section 3 may constantly be measuring an electroencephalogram, while the speech sound-wise summation section 6 or the group-wise summation section 7 may cut out any necessary event-related potential and apply a baseline correction thereto. With such construction, the presented-speech sound control section 11 does not need to send a trigger to the biological signal measurement section 50, but may send a trigger to the speech sound-wise summation section 6 or the group-wise summation section 7.

The visual stimulation presentation section 4 is a device which presents a character for speech sound intelligibility determination to the user 2. The visual stimulation presentation section 4 may be a television set or a display, for example. The visual stimulation presentation section 4 presents a character corresponding to the speech sound having been determined by the presented-speech sound control section 11 on the display surface.

The auditory stimulation presentation section 4 is a device which presents an audio for comfortableness determination to the user. The auditory stimulation presentation section 4 may be a speaker set or headphones, for example. The auditory stimulation presentation section 4 may be any arbitrary type. However, in order to enable correct determination, it needs to be adjusted so as to be able to precisely present an audio at a designated sound pressure. As a result, the auditory stimulation presentation section 4 is able to precisely present a monosyllabic audio that has been determined by the presented-speech sound control section 11.

The speech sound DB 12 is a database of speech sounds for use in hearing determination. FIG. 21 shows an exemplary database which is stored in the speech sound DB 12. For each speech sound, the speech sound DB 12 shown in FIG. 21 stores speech sound information of an audio file for presentation and a consonant label. As for the stored audios, it is assumed that the gain adjustment for each frequency has been completed based on a fitting method from audiograms of people suffering from hypacusia that were measured in advance. The types of speech sounds to be stored may be speech sounds that are in the 57S list or the 67S list. The consonant labels are utilized when determining a consonant that incurs a high probability of confusion by the user 2.

Moreover, the speech sound DB 12 contains data of a group(s) of a plurality of speech sounds. The data which is grouped in accordance with likelihood of confusion (how likely confusion is to occur, or probability of confusion) is utilized when determining the group that incurs a high probability of confusion by the user 2. The grouping may be a rough category, a medium category, and a fine category, for example.

The rough category concerns categorization as to vowels, unvoiced consonants, and voiced consonants, which are respectively represented as 0, 1, and 2. The medium category defines sub-categorization among unvoiced consonants and among voiced consonants. The unvoiced consonants can be categorized into the sa-row (medium category: 1) and the ta-/ka-/ha-rows (medium category: 2), whereas the voiced consonants can be categorized into the ra-/ya-/wa-rows (medium category: 1) and the na-/ma-/ga-/za-/da-/ba-rows (medium category: 2). The fine category can be divided into the na-/ma-rows (fine category: 1) and the za-/ga-/da-/ba-rows (fine category: 2), for example. As for likelihood of confusion, the inventors relied on "HOCHOKI FITTINGU NO KANGAEKATA (or "Concept of Hearing Aid Fitting") (Kazuoki KODERA, Shindan To Chiryosha, 1999, p. 172).

Moreover, the speech sound DB 12 contains summation group data for comfortableness determination, in order to enable group-by-group summation. The summation group data is utilized when differentiating between event-related potentials to be subjected to summation in the group-wise summation section 7. The summation groups may be annoyance and strife, for example. Annoyance is denoted as 0, 1, 2, 3, 4, or 5, corresponding to the amplitudes of the speech sound for determination. Strife is denoted as 0, 1, 2, 3, 4, or 5, corresponding to the frequencies of the speech sound for determination.

The presented-speech sound control section 11 determines the speech sound to be presented by referring to the speech sound DB 12, and sends information concerning the determined speech sound to the visual stimulation presentation section 4 and the auditory stimulation presentation section 5. Moreover, the presented-speech sound control section 11 sends triggers to the biological signal measurement section 3 according to respective points in time of presenting the audio and the character. Moreover, the presented-speech sound control section 11 sends information of the presented speech sound to the speech sound-wise summation section 6, and sends information of the presented speech sound, as well as the grouped data which the speech sound possesses, to the group-wise summation section 7. Moreover, the presented-speech sound control section 11 may also control the presentation of the determined speech sound by the visual stimulation presentation section 4 and the auditory stimulation presentation section 5.

In the present embodiment, it is assumed that the presented-speech sound control section 11 sends identical speech sound information to the visual stimulation presentation section 4 and the auditory stimulation presentation section 5.

In accordance with the content of the information of the speech sound for presentation received from the presented-speech sound control section 11, the speech sound-wise summation section 6 and the group-wise summation section 7 selectively use different portions of the waveform of the event-related potential received from the biological signal measurement section 3 for arithmetic mean.

From the biological signal measurement section 3, the speech sound-wise summation section 6 receives an event-related potential based on a trigger corresponding to a visual stimulation as a starting point. At this time, by utilizing the information of the speech sound for presentation received from the presented-speech sound control section 11, only the event-related potentials that are acquired in response to the presentation of the same speech sound are selectively used for arithmetic mean. Then, electroencephalogram data which has been subjected to a predetermined number of times of arithmetic mean for each speech sound is sent to the intelligibility determination section 8. Taking an arithmetic mean only for the same speech sound makes possible a determination of aural distinction of each speech sound.

From the biological signal measurement section 3, the group-wise summation section 7 receives an event-related potential based on a trigger corresponding to an auditory stimulation as a starting point. At this time, by utilizing the information of the speech sound for presentation and the grouped data possessed by the speech sound, which are received from the presented-speech sound control section 11, event-related potentials which are acquired in response to the presentation of speech sounds within the same group are selectively used for arithmetic mean. Then, electroencephalogram data which has been subjected to a predetermined number of times of arithmetic mean for each group is sent to the comfortableness determination section 9.

For example, the group-wise summation section 7 takes an arithmetic mean selectively of event-related potentials which are acquired in response to the presentation of speech sounds belonging to the same audio group (e.g., the rough category in FIG. 21).

The intelligibility determination section 8 distinguishes the arithmetic-meaned electroencephalogram waveform which has been received from the speech sound-wise summation section 6, and determines the speech sound intelligibility for each speech sound. The result of speech sound intelligibility determination is sent to the hearing determination result DB 10.

Figure 22:
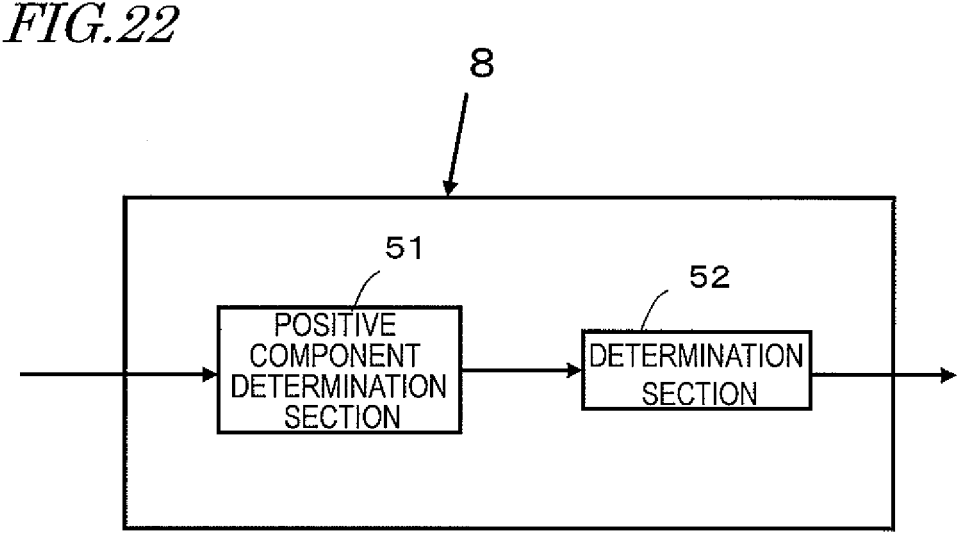
FIG. 22 is a diagram showing the construction of an intelligibility determination section 8.

FIG. 22 shows the construction of the intelligibility determination section 8.

As shown in FIG. 22, the intelligibility determination section 8 includes a positive component determination section 51 and a determination section 52.

The positive component determination section 51 receives the arithmetic-meaned electroencephalogram waveform from the speech sound-wise summation section 6, and determines the presence or absence of a positive component at a latency of about 300 ms or about 500 ms in the arithmetic mean waveform. The presence or absence of the positive component is distinguished by the following method. For example, the positive component determination section 51 compares a maximum amplitude at a latency from 200 ms to 400 ms or a zone average potential at a latency from 200 ms to 400 ms against a predetermined threshold value. Then, if the maximum amplitude at a latency from 200 ms to 400 ms or the zone average potential at a latency from 400 ms to 600 ms is greater than the threshold value, the case is distinguished as "the positive component is present"; and if it is smaller, "the positive component is absent".

Receiving the presence or absence of the positive component from the positive component determination section 51, the determination section 52 determines intelligibility based on the presence or absence of the positive component, and sends the determination result to the hearing determination result DB 10.

The comfortableness determination section 9 distinguishes the waveform of the arithmetic-meaned electroencephalogram (event-related potential) received from the group-wise summation section 7, and determines the comfortableness for each group. The comfortableness determination section 9 sends the result of comfortableness determination to the hearing determination result DB 10.

Figure 23:
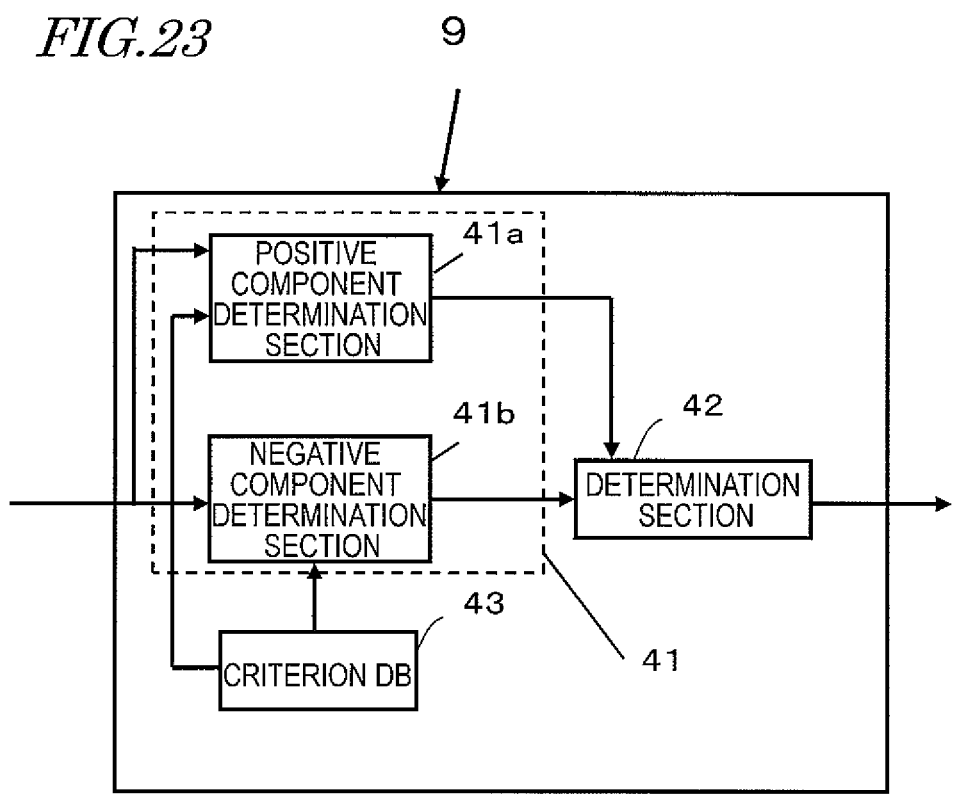
FIG. 23 is a diagram showing the construction of a comfortableness determination section 9.

FIG. 23 shows the construction of the comfortableness determination section 9.

As shown in FIG. 23, the comfortableness determination section 8 includes a characteristic component determination section 41, a determination section 42, and a criterion database (DB) 43.

The characteristic component determination section receives the waveform of the arithmetic-meaned electroencephalogram (event-related potential) from the group-wise summation section 7, and data of a latency and a threshold value for negative component detection and positive component detection from the criterion DB 43.

The characteristic component determination section includes a positive component determination section 41a and a negative component determination section 41b.

In the case of determining strife, the positive component determination section 41a determines whether a positive component is present at a latency of about 750 ms in the arithmetic mean waveform. The presence or absence of the positive component is distinguished by the following method. For example, the positive component determination section 41a compares a maximum amplitude at a latency from 600 ms to 900 ms or a zone average potential at a latency from 600 ms to 900 ms against a predetermined threshold value. The "predetermined threshold value" when using a zone average potential may be 2.36 µV, i.e., a median between the zone average potentials for "high strife" and "low strife" obtained in the aforementioned experiment, this serving as a threshold value for the presence or absence of the positive component of a generic user. Then, if the zone average potential is greater than the threshold value, the positive component determination section 41a may distinguish the case as "the positive component is present", and if it is smaller, "the positive component is absent". The aforementioned "latency of about 750 ms" and threshold value are set based on the data received from the criterion DB 43.

In the case of determining annoyance, the negative component determination section 41b determines the presence or absence of a negative component at a latency of about 200 ms in the arithmetic mean waveform. The presence or absence of the negative component is distinguished by the following method. For example, the negative component determination section 41b compares a maximum amplitude at a latency from 100 ms to 300 ms or a zone average potential at a latency from 100 ms to 300 ms against a predetermined threshold value. Then, if the zone average potential is greater than the threshold value, the negative component determination section 41b may distinguish the case as "the negative component is present", and if it is smaller, "the negative component is absent". Alternatively, the negative component determination section 41b may compare the latency of a negative potential peak at a latency from 100 ms to 300 ms against a predetermined threshold value. Then, if the peak latency of the negative potential is shorter than the predetermined threshold value, the negative component determination section 41b may distinguish the case as "the negative component is present"; if the peak latency is equal to or greater than the predetermined threshold value, the negative component determination section 41b may distinguish the case as "the negative component is absent". The "predetermined threshold value" may be 218 ms, which is a median of the latency of the negative component concerning "annoying"/"not annoying" that was obtained in the experiment as a threshold value for the presence or absence of the negative component of a generic user. Alternatively, by relying on a similarity level (e.g., correlation coefficient) with a predetermined template which is generated from the waveform of a typical negative component signal at a latency of about 200 ms, the negative component determination section 41b may distinguish any similar case as "the negative component is present", and any non-similar case as "the negative component is absent". The predetermined threshold value or template may be calculated or generated from a previously-acquired negative component waveform of a generic user. The aforementioned latency (e.g., "about 200 ms") and threshold value are set based on the data received from the criterion DB 43.

Receiving the presence or absence of the positive component and the negative component from the characteristic component determination section 41, the determination section determines comfortableness based on the presence or absence of the positive component and the negative component, and sends the determination results to the hearing determination result DB 10.

The hearing determination result DB 10 is database for storing the results of hearing determination. It receives determination results from the intelligibility determination section 8 and the comfortableness determination section 9, and stores them as results of hearing determination.

Hereinafter, with reference to FIG. 24 to FIG. 26, a processing procedure of the aforementioned hearing determination system 100 will be described in detail.

First, with reference to FIG. 24, an overall processing procedure performed by the hearing determination system 100 of FIG. 16 will be described. FIG. 24 is a flowchart showing a procedure of processing by the hearing determination system 100.

At step S10, the biological signal measurement section 3 begins measurement of an electroencephalogram of the user 2. Electroencephalogram measurement is continuously performed throughout the subsequent steps.

At step S11, the presented-speech sound control section 11 determines a monosyllabic speech sound to be presented by referring to the speech sound DB 12. The auditory stimulation presentation section 5 presents an audio of the determined speech sound to the user 2. At the same time as presenting the audio, the presented-speech sound control section 11 sends a trigger for presenting an audio stimulation to the biological signal measurement section 3, and sends information of the speech sound for presentation and the grouped data possessed by the speech sound to the group-wise summation section 7. At this time, regarding the consonant labels, rough category, medium category, and fine category shown in FIG. 21, grouped data is defined by the label and numbers corresponding to each speech sound. For example, if the grouping is "rough category" and the speech sound "あ (a)" is to be presented, then the presented-speech sound control section 11 sends the grouped data "0" to the group-wise summation section 7.

At step S12, by referring to the speech sound DB 12, the presented-speech sound control section 11 determines a character to be presented following the auditory stimulation at step S11. The visual stimulation presentation section 4 presents the determined character to the user 2. For example, the visual stimulation is presented 1 second (1000 ms) after the auditory stimulation is presented. At the same time as presenting the character, the presented-speech sound control section 11 sends to the biological signal measurement section 3 a trigger for presenting a visual stimulation, and sends information of the presented speech sound to the speech sound-wise summation section 6.

At step S13, upon receiving the trigger from the presented-speech sound control section 11, the biological signal measurement section 3 cuts out an event-related potential from e.g. −200 ms to 1000 ms from the measured electroencephalogram, based on the trigger as a starting point. Then, an average potential from −200 ms to 0 ms is determined, and the resultant event-related potential is subjected to baseline correction so that this average potential becomes 0 µV. At this time, an event-related potential based on the trigger corresponding to the auditory stimulation as a starting point is sent to the group-wise summation section 7, and an event-related potential based on the trigger corresponding to the visual stimulation as a starting point is sent to the speech sound-wise summation section 6.

At step S14, the group-wise summation section 7 takes an arithmetic mean of the event-related potential cut out at step S13 for each group, based on the speech sound for presentation and the grouped data possessed by the speech sound received from the presented-speech sound control section 11. For example, the consonant labels, rough category, medium category, fine category, annoyance, and strife illustrated in FIG. 21 define the grouping. If the grouping is set to "rough category" and the speech sound "あ (a)" is presented, then the speech sound "あ (a)" and the grouped data "0" are sent from the presented-speech sound control section 11. The group-wise summation section 7 refers to the grouped data "0", and stores this waveform. Thereafter, whenever speech sounds having the same grouped data ("い (i)", "う (u)", "え (e)", "お (o)") are presented, the group-wise summation section 7 takes an arithmetic mean of these waveforms.

At step S15, based on the information of the speech sound for presentation which is received from the presented-speech sound control section 11, the speech sound-wise summation section 6 takes an arithmetic mean of the event-related potential cut out at step S13 for each speech sound.

Step S16 defines a branching as to whether presentation has been completed for the one set of speech sounds that was to be subjected to hearing determination. If it is not complete, the process returns to step S11; if it is complete, the process proceeds to step S17.

Step S17 defines a branching as to whether presentation has been completed for the number of speech sound sets needed for determination. If it is not complete, the process returns to step S11; if it is complete, the process proceeds to step S18.

At step S18, from the group-wise summation section the comfortableness determination section 9 receives electroencephalogram data of which an arithmetic mean has been taken for each group, and determines comfortableness for each group. Then, the result of comfortableness determination is sent to the hearing determination result DB 12. Hereinafter, details of step S18 will be described with reference to FIG. 25.

Figure 24:
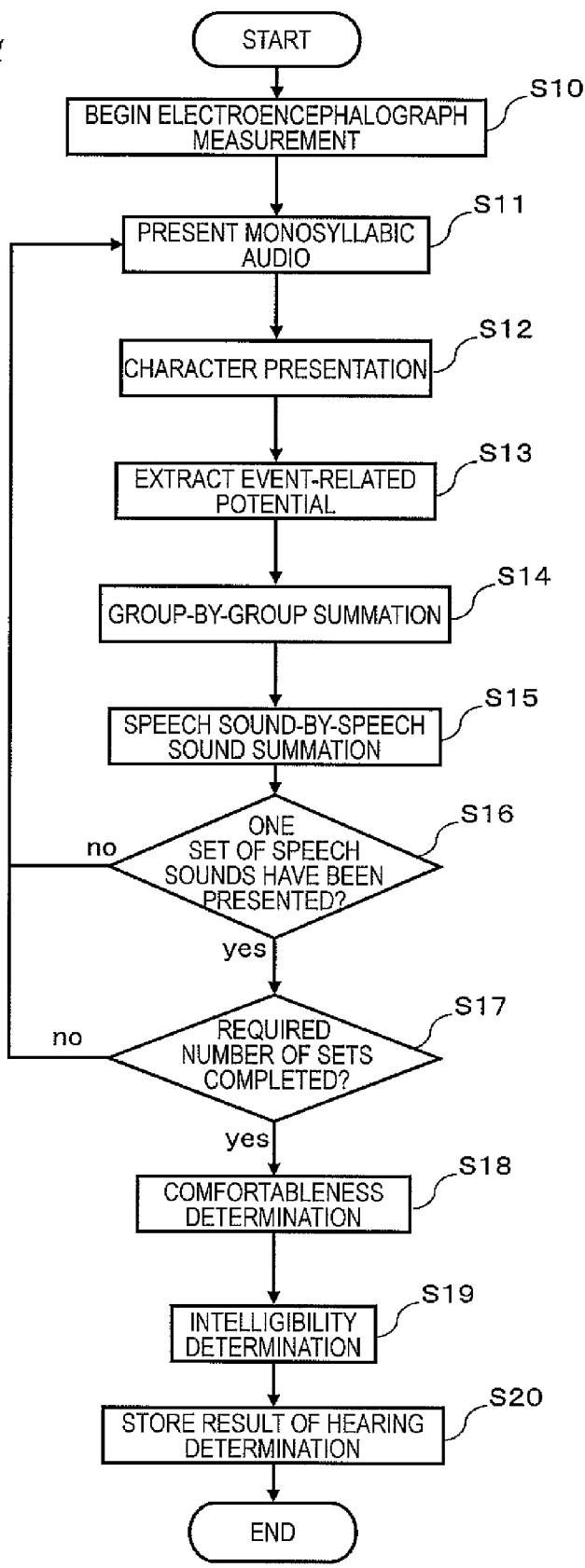
FIG. 24 is a flowchart showing a procedure of processing by the hearing determination system 100.
Figure 25:
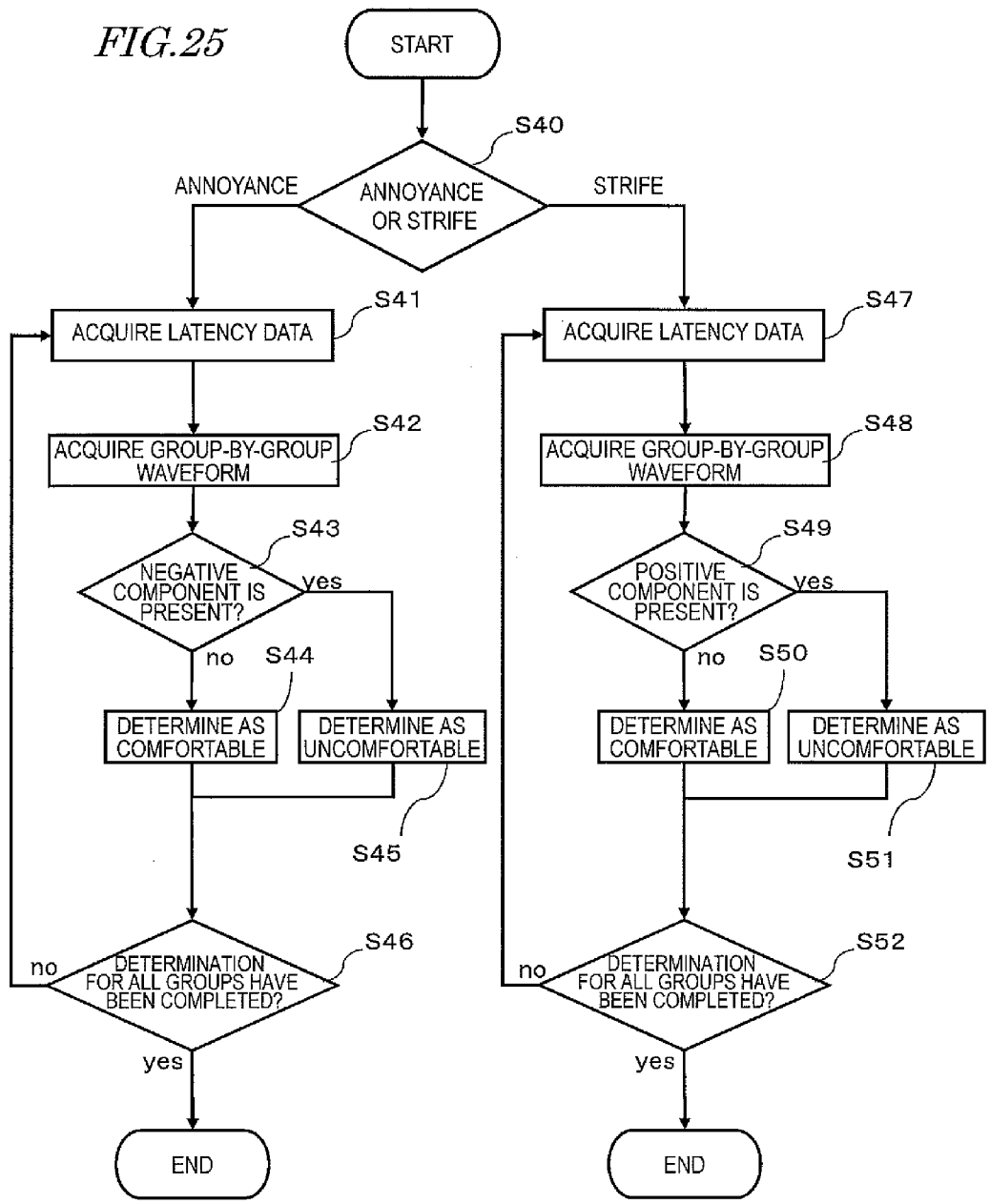
FIG. 25 is a flowchart showing a detailed procedure of processing of step S18 in FIG. 24.
Figure 26:
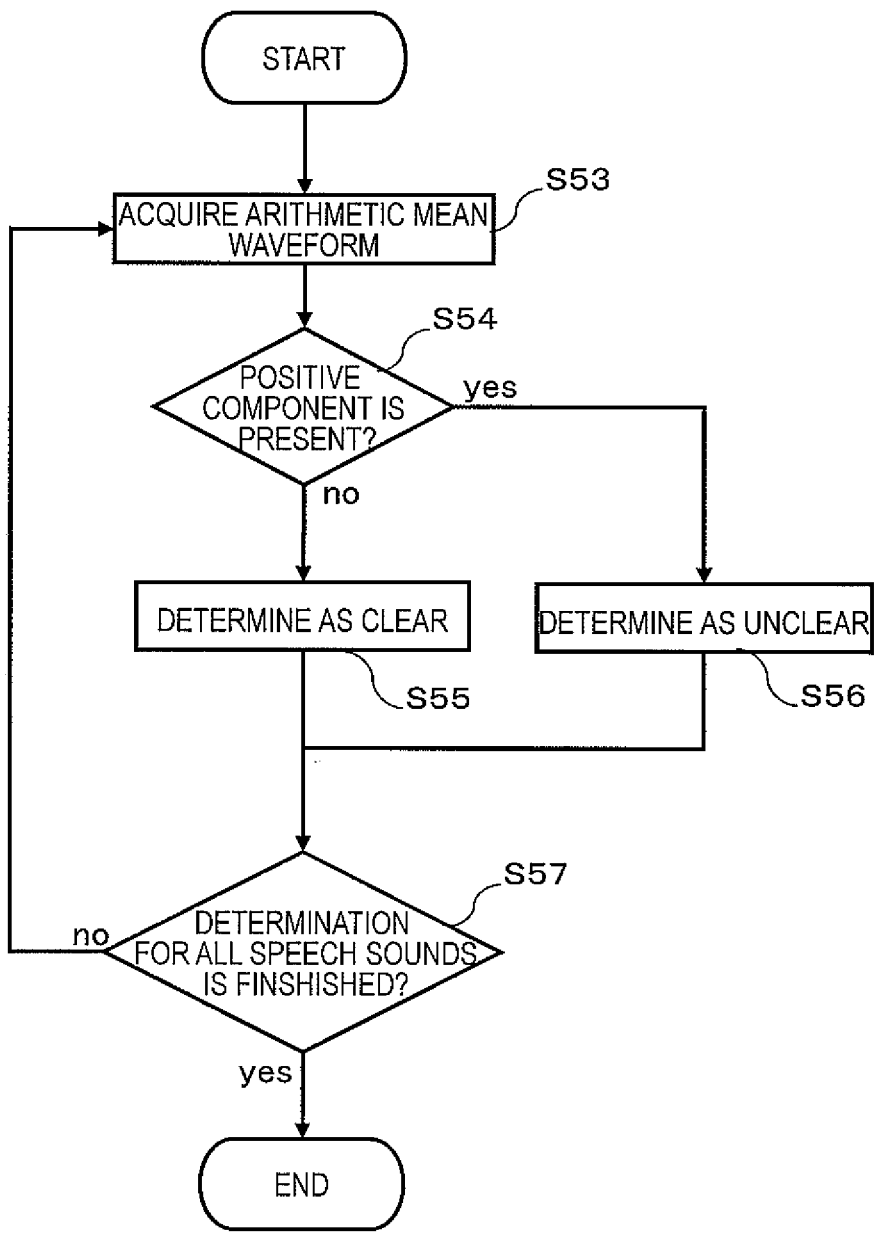
FIG. 26 is a flowchart showing a detailed procedure of processing of step S19 in FIG. 24.

FIG. 25 is a flowchart showing a detailed procedure of processing of step S18 of FIG. 24.

At step S40, the characteristic component determination section 41 determines whether the item of determination should be "annoyance" or "strife". In other words, receiving data identifying the item of determination from the group-wise summation section 7, the characteristic component determination section 41 proceeds to the process of step S41 if the item of determination is annoyance, or to the process of step S47 if the item of determination is strife.

At step S41, the characteristic component determination section 41 receives latency data for negative component detection from the criterion DB 43.

At step S42, the characteristic component determination section 41 receives electroencephalogram data of which an arithmetic mean has been taken for each group.

At step S43, the negative component determination section 41b determines whether a negative component is present at a latency of about 200 ms. If a negative component is not detected by the negative component determination section 41b, the process proceeds to step S44; if a negative component is detected, the process proceeds to step S45.

At step S44, upon being informed by the negative component determination section 41b that no negative component is present at a latency of about 200 ms in the speech sound presented at step S11, the determination section 42 makes a "comfortable" determination, and accumulates this determination result.

At step S45, upon being informed by the negative component determination section 41b that a negative component is present at a latency of about 200 ms in the speech sound presented at step S11, the determination section 42 makes an "uncomfortable" determination, and accumulates this determination result.

At step S46, the determination section 42 determines whether comfortableness determination has been completed for all of the groups to be subjected to comfortableness determination. If comfortableness determination is not complete, the process returns to step S41; if it is complete, the process is ended.

Next, a process of the case where strife is the item of determination will be described.

At step S47, the characteristic component determination section 41 receives latency data for positive component detection from the criterion DB 43.

At step S48, the characteristic component determination section 41 receives electroencephalogram data of which an arithmetic mean has been taken for each group.

At step S49, the positive component determination section 41a determines whether a positive component is present at a latency of about 200 ms. If no positive component is detected by the positive component determination section 41a, the process proceeds to step S50; if a negative component is detected, the process proceeds to step S51.

At step S50, upon being informed by the positive component determination section 41a that no positive component is present at a latency of about 750 ms in the speech sound presented at step S11, the determination section 42 makes a "comfortable" determination, and accumulates this determination result.

At step S51, upon being informed by the positive component determination section 41a that a positive component is present at a latency of about 750 ms in the speech sound presented at step S11, the determination section 42 makes an "uncomfortable" determination, and accumulates this determination result.

At step S52, the determination section 42 determines whether comfortableness determination has been completed for all of the groups to be subjected to comfortableness determination. If comfortableness determination is not complete, the process returns to step S47; if it is complete, the process is ended.

FIG. 24 is referred to again.

At step S18, from the speech sound-wise summation section 6 the intelligibility determination section 8 receives electroencephalogram data of which an arithmetic mean has been taken for each speech sound, and determines the speech sound intelligibility for each speech sound. Then, the result of speech sound intelligibility determination is sent to the hearing determination result DB 12. Hereinafter, details of step S19 will be described with reference to FIG. 26.

At step S53, the positive component determination section 51 receives electroencephalogram data of which an arithmetic mean has been taken for each group.

Step S54 defines a branching as to whether a positive component at a latency of about 300 ms is detected by the positive component determination section 51. If no positive component is detected, the process proceeds to step S53; if the positive component is detected, the process proceeds to step S54.

At step S55, with respect to the group informed from the presented-speech sound control section 11 at step S11, upon being informed by the positive component determination section 41 that a positive component is present at a latency of about 300 ms, the determination section 52 makes a "clear" determination, and accumulates this determination result.

At step S56, with respect to the group informed from the presented-speech sound control section 11 at step S11, upon being informed by the positive component determination section 41 that no positive component is present at a latency of 300 ms, the determination section 52 makes an "unclear" determination, and accumulates this determination result.

Step S57 defines a branching as to whether intelligibility determination has been completed for all of the speech sounds to be subjected to intelligibility determination. If it is not complete, the process returns to step S53; if it is complete, the speech sound intelligibility determination is ended.

At step S20, the hearing determination result DB 10 receives from the intelligibility determination section 8 determination results in which each speech sound is determined as clear or unclear, and receives from the comfortableness determination section 9 determination results in which each group is determined as comfortable or uncomfortable. Then, these results are accumulated in the database.

Now, effects of selectively using different portions of the electroencephalogram for summation depending on the item of determination in the above-illustrated hearing determination system 100 will be described.

Hereinafter, in discussing the number of presentations of audios/characters, the number of presentations will be expressed in terms of a speech sound set and a required number of sets.

A "speech sound set" is defined as a set of speech sounds to be subjected to batch determination. For example, in the case where the 20 speech sounds in the 67S list are to be presented, these 20 speech sounds constitute one speech sound set, which result in 20 times of presentation. By repeating this speech sound set as many times as the required number of sets, an arithmetic mean for the electroencephalogram can be achieved.

A "required number of sets" is defined as the number of speech sound sets required for achieving a number of summations that suffices for both of speech sound intelligibility determination and comfortableness determination. In the aforementioned conventional example which does not employ selective use of different portions of the electroencephalogram, the required number of sets is 20. Note that the total number of presentations equals (the number of speech sounds in the speech sound set)×(required number of sets).

FIG. 27 is a diagram showing exemplary results of intelligibility determination, and, exemplary results of comfortableness determination for different groups into which speech sounds are classified.

The effects of selectively using different portions of the electroencephalogram according to the present disclosure will be described with respect to an exemplary case where speech sound intelligibility determination is made for the 20 speech sounds of the speech sound set (20 speech sounds, 67S list) as shown in FIG. 27 and comfortableness determination is made in a batch based on the rough category shown in FIG. 21. As described earlier, the rough category is divided into vowels, unvoiced consonants, and voiced consonants. In this case, the 20 speech sounds in the 67S list include 3 speech sounds from the vowel group, 9 speech sounds from the voiced consonant group, and 8 speech sounds from the unvoiced consonant group. In the following calculation of the required number of sets, it is assumed that 5 summations are required to make speech sound-by-speech sound determinations, and 20 summations are required to make comfortableness determination.

When calculating the required number of sets, it is necessary to consider a number of sets that is necessary for each of the speech sound intelligibility determination and the comfortableness determination separately.

Speech sound intelligibility determination is to be made for the 20 speech sounds. Therefore, by presenting the speech sound set (20 speech sounds) in an equivalent of 5 sets, 5 summations will have been incurred, whereby speech sound intelligibility determination is realized.

20 speech sounds:1 speech sound×5 sets=5 summations

On the other hand, comfortableness determination is to be made with respect to the three groups. For each of the three groups, a required number of sets is found as follows.

vowels:3 speech sounds×7 sets=21 summations voiced consonants:9 speech sounds×3 sets=27 summations unvoiced consonants:8 speech sounds×3 sets=24 summations Thus, the 20 summations which is necessary for comfortableness determination is attained with 7 sets for vowels, 3 sets for voiced consonants, 3 sets for unvoiced consonants.

Now, in order to find a number of summations which suffices for both determinations, the largest required number of sets should prevail. Therefore, in this exemplary case, the required number of sets is determined to be 7 according to the vowel group, which has the smallest number of speech sounds within the group.

As this result indicates, the required number of sets is greatly reduced from 20 to 7. In this case, as shown in FIG. 27, a clear/unclear determination result is obtained for each speech sound (intelligibility), whereas a comfortable/uncomfortable determination result is obtained for each audio group (comfortableness).

Each determination result (○, X) in FIG. 27 is a result of detecting a relevant component in the arithmetic mean waveform, and indicates presence or absence of the component. For example, in speech sound intelligibility determination, presence or absence of the positive component is determined, and those for which the positive component is determined as absent are rated as ○ (clear), whereas those for which the positive component is determined as present are rated as X (unclear).

Similarly, in comfortableness determination, the presence or absence of a relevant component is determined, and those for which the relevant component is determined as absent are rated as ○ (comfortable), whereas those for which the relevant component is determined as present are rated as X (uncomfortable).

By assuming that the presented speech sounds are 20 speech sounds, there are three levels of sound pressure at which audios may be presented, and there are 3 seconds of interval between audio stimulations in the aforementioned example, the hearing determination time when a hearing aid is not worn/when a hearing aid is worn will be considered. Prior to the present technique, the required number of sets would have been 20 times, and the determination time would have been:

20 speech sounds×three levels×3 seconds×2 patterns× 20 sets=7200 seconds(2 hours).

On the other hand, when the present technique is adopted, it will be:

20 speech sounds×three levels×3 seconds×2 patterns×7 sets=2520 seconds(42 minutes).

Thus, the determination time is reduced from 2 hours to 42 minutes, which is a considerable reduction in time.

With the hearing determination system 100 of the present embodiment, the number of audio/character presentations is reduced, and hearing determination is realized in a short period of time. As a result, the amount of time required for a hearing determination which is conducted at a hearing aid shop is reduced, for example, thus reducing the trouble of a hearing aid user.

In the present example, it is assumed that comfortableness is represented by an annoyance determination result. However, comfortableness determination may be conducted so that comfortableness is represented by a strife determination result, or comfortableness is represented by both of annoyance and strife determination results, as has been discussed in the electroencephalogram measurement experiments.

In the biological signal measurement section 3, the level and polarity of any characteristic component of a measured event-related potential may vary depending on the position at which electrodes for electroencephalogram measurement are worn, and the settings of the reference electrode and probe electrode. However, based on the following description, those skilled in the art should be able to make appropriate modifications in accordance with the particular setting of the reference electrode and probe electrode to detect a characteristic component of an event-related potential and perform hearing determination. Such variants are also encompassed by the present disclosure.

Although grouped data is retained by the speech sound database in the present example, this data may be kept in the group-wise summation section 7 instead.

In the group-wise summation section 7, the audio groups in taking group-by-group summations may be established so that any speech sounds sharing the same consonant are in one group, or that any speech sounds having the same likelihood of confusion (the rough category, medium category, or fine category in the grouping illustrated in FIG. 21) are in one group. In the case where an arithmetic mean is taken of speech sounds sharing the same consonant, it becomes possible to determine which consonant induces low comfortableness. In the case where an arithmetic mean is taken of each group of likelihood of confusion, group-by-group determination becomes possible; e.g., between a group of voiced consonants and a group of unvoiced consonants, there is a high comfortableness for voiced consonants and a low comfortableness for unvoiced consonants. In the case of taking an arithmetic mean in a consonant-by-consonant or group-by-group manner, an arithmetic mean waveform is obtained through a number of summations which is equal to the number of speech sounds belonging to the same group. Therefore, as compared to the comfortableness determination associated with a large required number of summations, determination with a smaller number of audio/character presentations is enabled.

When selecting the presented speech sounds from the speech sound DB 12, only as many as the required number of summations may be selected for presentation. For example, in the case of making a batch determination based on three audio groups (vowels: 3 speech sounds, voiced consonants: 9 speech sounds, unvoiced consonants: 8 speech sounds) as illustrated above, the required number of sets was 7 sets. In this case, the required number of sets for the voiced consonant group and the unvoiced consonant group is 3 sets, but these groups are presented in an equivalent of 7 sets, thus incurring a long determination time. When the overall number of sets is larger than the required number of sets for each group as in this case, the number of sets may be curtailed; however, the required number of sets for speech sound intelligibility is 5 sets in this case, and therefore 5 sets is the minimum possible value for realizing both determinations. Accordingly, the required number of sets for the voiced consonant group and the unvoiced consonant group would be five. Therefore, presentations may be ended as soon as the required number of summations is reached for each group, e.g., 7 sets for the vowel group, and 5 sets for the voiced consonant group or the unvoiced consonant group. Thus, in the case where only as many presentations as the required number of summations are made, the effect of time reduction according to the present disclosure is enhanced.

Note that the presented speech sounds may be randomly selected from the speech sound DB 12, or speech sounds of a specific consonant or group may be exclusively selected. In a similar example to the above, where a batch determination is made based on three audio groups (vowels: 3 speech sounds, voiced consonants: 9 speech sounds, unvoiced consonants: 8 speech sounds), a case of repeating a speech sound in a specific group (e.g., the vowel "ア (a)") as shown in FIG. 28 is considered. In this case, the aforementioned method of calculation for the required number of sets will dictate that 20 summations are achieved in 5 sets. Therefore, the number of sets required for all determinations is 5 sets. Thus, by adjusting the speech sounds within the group, the effect of time reduction according to the present disclosure is enhanced.

Note that the presented speech sounds may be selected by a combination of a method of randomly selecting from the speech sound DB 12 or exclusively selecting speech sounds of a specific consonant or group and a method of presenting only as many as the required number of summations. Combining two methods will enable determination with the smallest necessary number of sets, so that hearing determination can be finished in the shortest determination time that is possible in the present system.

In the presented-speech sound control section 11, the number of sets that is necessary for each item of determination may be determined from the magnitude of an electroencephalogram signal component of the user 2 which is measured by the biological signal measurement section 3. By determining the number of sets from the magnitude of the signal component, it becomes possible to realize hearing determination in the shortest determination time that is possible for the user, while achieving a desired accuracy.

In the presented-speech sound control section 11, the speech sounds may be determined by receiving information of speech sounds which are yet to be determined or to be determined again from the hearing determination system 100.

In the intelligibility determination section 8 and the comfortableness determination section 9, distinction of the positive component or the negative component may be performed comparison against a threshold value or comparison against a template.

Note that the hearing determination apparatus 1 may be implemented as a piece of hardware (e.g., a DSP) consisting of a semiconductor circuit having a computer program incorporated therein. Such a DSP can realize all functions of the aforementioned CPU 30, memory 31, audio controller 32, and graphics controller 33 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 19 (e.g., a PC) is able to function as the hearing determination apparatus 1 according to the present embodiment. Note that the speech sound DB 12 does not need to be stored in the memory 31, but may be stored on a hard disk (not shown) which is connected to the bus 34.

Since the hearing determination apparatus 1 of the present embodiment is portable, a user can actually bring a hearing aid and the hearing determination apparatus 1 to an acoustic environment where the hearing aid is to be used, e.g., home or a workplace, and make a hearing determination there, for example. This makes it possible to determine hearing in daily life more precisely.

Although FIG. 18 illustrates the visual stimulation presentation section 4 as a display, the visual stimulation presentation section 4 may be a television set. When adopting a construction of being connected to a television set, the hearing determination apparatus 1 may only include well-known circuitry for generating a video signal for displaying video on the television set and terminals for outputting the video signal. As a result, an easily-portable hearing determination apparatus 1 with a simplified construction can be obtained, which enables hearing determination in an environment where the user will be using a hearing aid. In this case, furthermore, the auditory stimulation presentation section 5 may be the loudspeakers which a television set is usually equipped with. Thus, a simplified construction is realized, with only generation circuits and output terminals for the video signal and audio signal to the television set being provided.

Although FIG. 18 illustrates the auditory stimulation presentation section 5 as a speaker set, the auditory stimulation presentation section 5 may instead be headphones. Use of headphones facilitates transportation, thus enabling a hearing determination in an environment where the user will be using a hearing aid.

Although the present embodiment illustrates that the result of comfortableness determination and the result of intelligibility determination are accumulated in the hearing determination result DB 10, the results may not be accumulated. For example, in the case where the result accumulating DB 80 is provided externally to the hearing determination apparatus 1, the determination results by the positive component determination section 60 and the negative component determination section 65 may simply be output. Each determination result may be utilized as information concerning comfortableness of speech sound listening.

In the present specification, the event-related potential waveforms are subjected to summation or arithmetic mean, this being in order to confirm appearance of a component that reflects subjective perception concerning intelligibility in the event-related potential. However, this is an example. Depending on the method of characteristic amount extraction (e.g., wavelet transformation for the waveforms) or the method of identification (e.g., support vector machine learning), distinction of a positive component or a negative component is possible with no summations or only a small number of summations. For example, the speech sound-wise summation section 6 may be omitted.

As a result, hearing determination can be realized in an acoustic environment in which the user will be using the hearing aid.

The present embodiment has been illustrated based on hearing determination for the Japanese language. However, it may be English or Chinese so long as the speech sounds are monosyllabic. In the case of English, for example, monosyllabic words may be presented, and a determination may be made on a word-by-word basis. FIG. 29 shows an exemplary result of determining strife, annoyance, and intelligibility for different monosyllabic words.

3. Embodiment 2

Embodiment 1 illustrates an example where speech sound intelligibility and comfortableness are determined simultaneously.

The present embodiment illustrates a hearing determination system which determines comfortableness but does not determine speech sound intelligibility.

Figure 30:
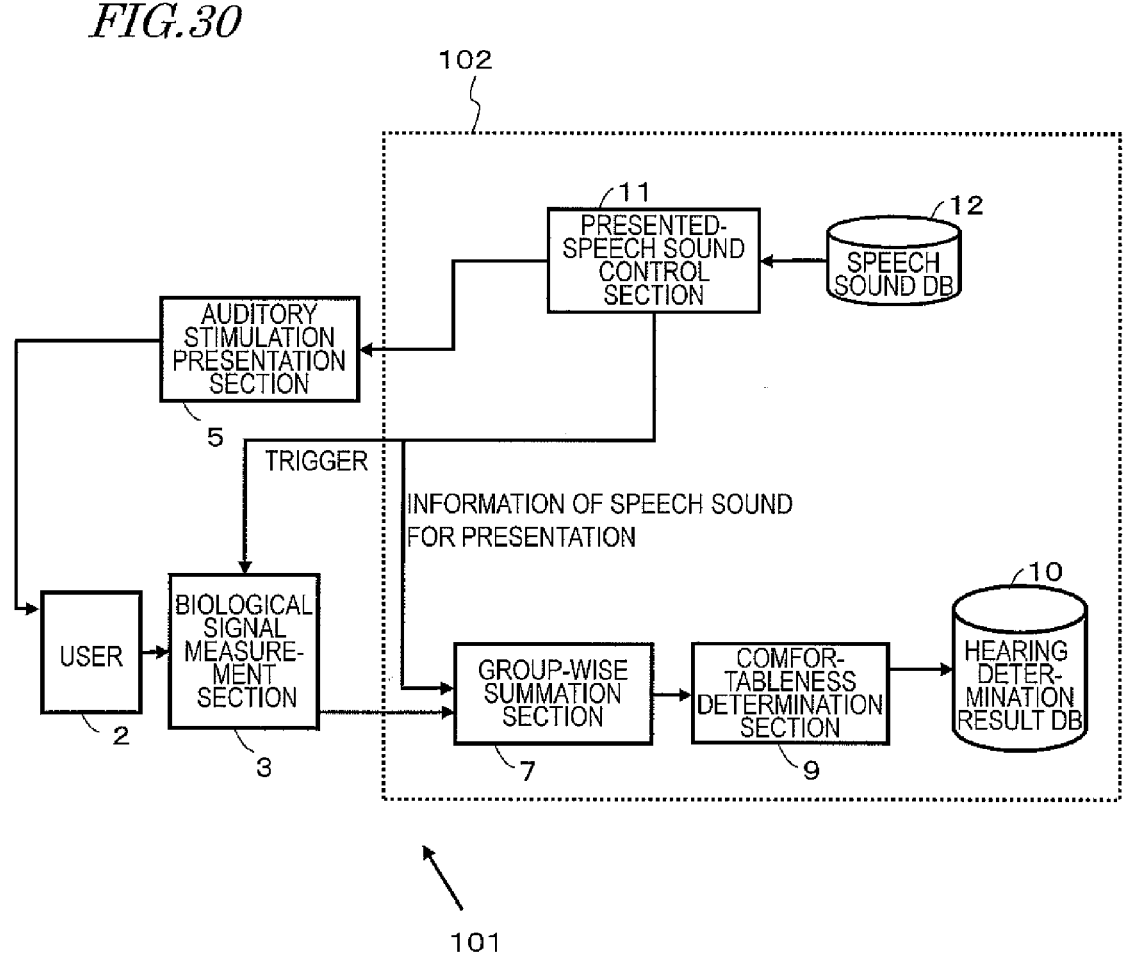
FIG. 30 is a block configuration diagram of a hearing determination system 101 according to Embodiment 2.

FIG. 30 shows a block configuration diagram of a hearing determination system 101 according to the present embodiment. The hearing determination system 101 differs from the hearing determination system 100 of Embodiment 1 with respect to the construction of the hearing determination apparatus 102. Specifically, the visual stimulation presentation section 4, the speech sound-wise summation section 6, and the intelligibility determination section 8 of the hearing determination apparatus 1 according to Embodiment 1 are omitted from the hearing determination apparatus 102 of the present embodiment. Due to these differences in construction, the presented-speech sound control section 11 do not output any instruction for outputting a character corresponding to a speech sound as a visual stimulation, or send a trigger based on a visual stimulation as a starting point to the biological signal measurement section 3. Otherwise, it is similar to the hearing determination system 100 of Embodiment 1.

Figure 31:
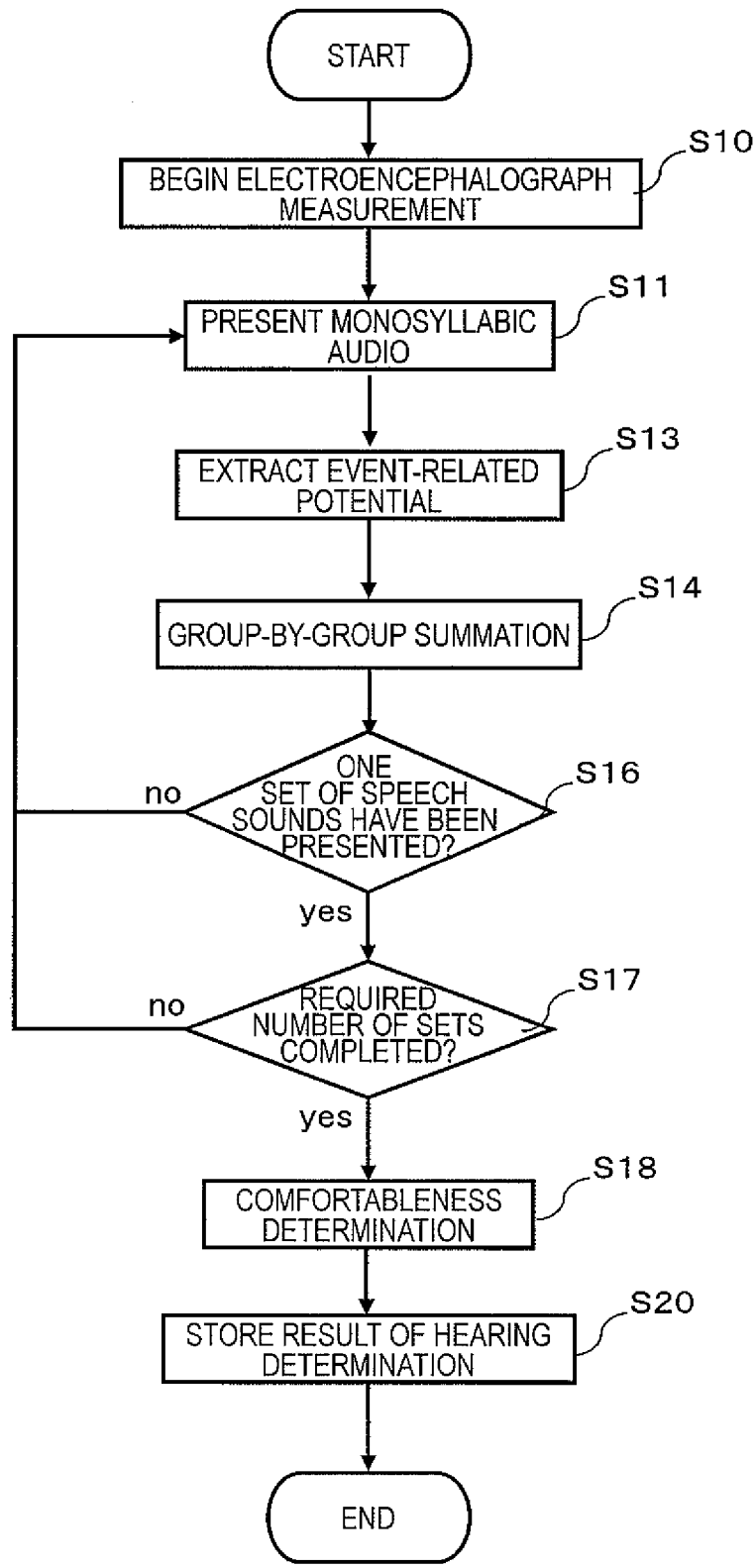
FIG. 31 is a flowchart showing an overall processing procedure which is performed in the hearing determination system 101 of Embodiment 2.

FIG. 31 is a flowchart showing an overall processing procedure which is performed in the hearing determination system 101 of FIG. 30. This flowchart differs from the flowchart (FIG. 24) of the hearing determination system 100 according to Embodiment 1 in that steps S12, S15, and S19 of FIG. 24 are omitted.

The description of Embodiment 1 is relied on for any common component elements and process operations.

In the hearing determination system 101 and the hearing determination apparatus 102 of the present embodiment, intelligibility determination is omitted, so that there is no need to distinguish speech sounds, but only comfortableness determination may be performed. As a result, determination results can be obtained in shorter periods of time.

4. Variants of Embodiments 1 and 2

In the hearing determination system 100 of the earlier embodiment, at the positive component determination section 51 in the intelligibility determination section 8 (FIG. 22) and at the positive component determination section 41*a* and negative component determination section 41*b* in the comfortableness determination section 9 (FIG. 23), the presence or absence of a positive component and the presence or absence of a negative component are respectively determined by using threshold values calculated from the positive component/negative component of a generic user or templates of positive component/negative components of a generic user.

However, since event-related potential waveforms have large individual differences, accurate determinations of strife and annoyance may be difficult to make through distinction on that basis.

Accordingly, prior to comfortableness determination of speech sound listening, a calibration is made for measuring the traits of a positive component at a latency of about 750 ms and a negative component at a latency of about 200 ms of each user, and comfortableness may be determined based on the component traits of each individual person. The user may be allowed to choose whether or not to make a calibration.

The method of calibration may be as follows.

The presented-speech sound control section 11 determines a speech sound type by referring to the speech sound DB 12. Then, regarding monosyllabic audio presentation, the presented-speech sound control section 11 sets either (1) a sound pressure level at which the user can hear without strife but which is felt as "annoying", or (2) a sound pressure level at which strife is required but which is felt as "not annoying". Then, an audio is presented to the user 2 via the auditory stimulation presentation section 5.

Then, the speech sound-wise summation section 6 and the group-wise summation section 7 each take an arithmetic mean of the event-related potential measured by the biological signal measurement section 50 for each sound pressure level.

Finally, the speech sound-wise summation section 6 and the group-wise summation section 7 each store a trait parameter for each sound pressure level. More specifically, from the arithmetic mean waveform, the speech sound-wise summation section 6 and the group-wise summation section 7 each calculate trait parameters to be used for distinction at the positive component determination section 51, and the positive component determination section 41a and the negative component determination section 41b. For example, in the case where each trait parameter is a zone average potential, an average potential in a predetermined zone is calculated. Then, the respective threshold values are stored in the criterion DB 43 or the like. The average values thus obtained can be considered representative of traits that are unique to that user.

Using threshold values that are obtained in this manner enables a more precise determination which takes into consideration the individual differences of each individual user.

5. Embodiment 3

Figure 32:
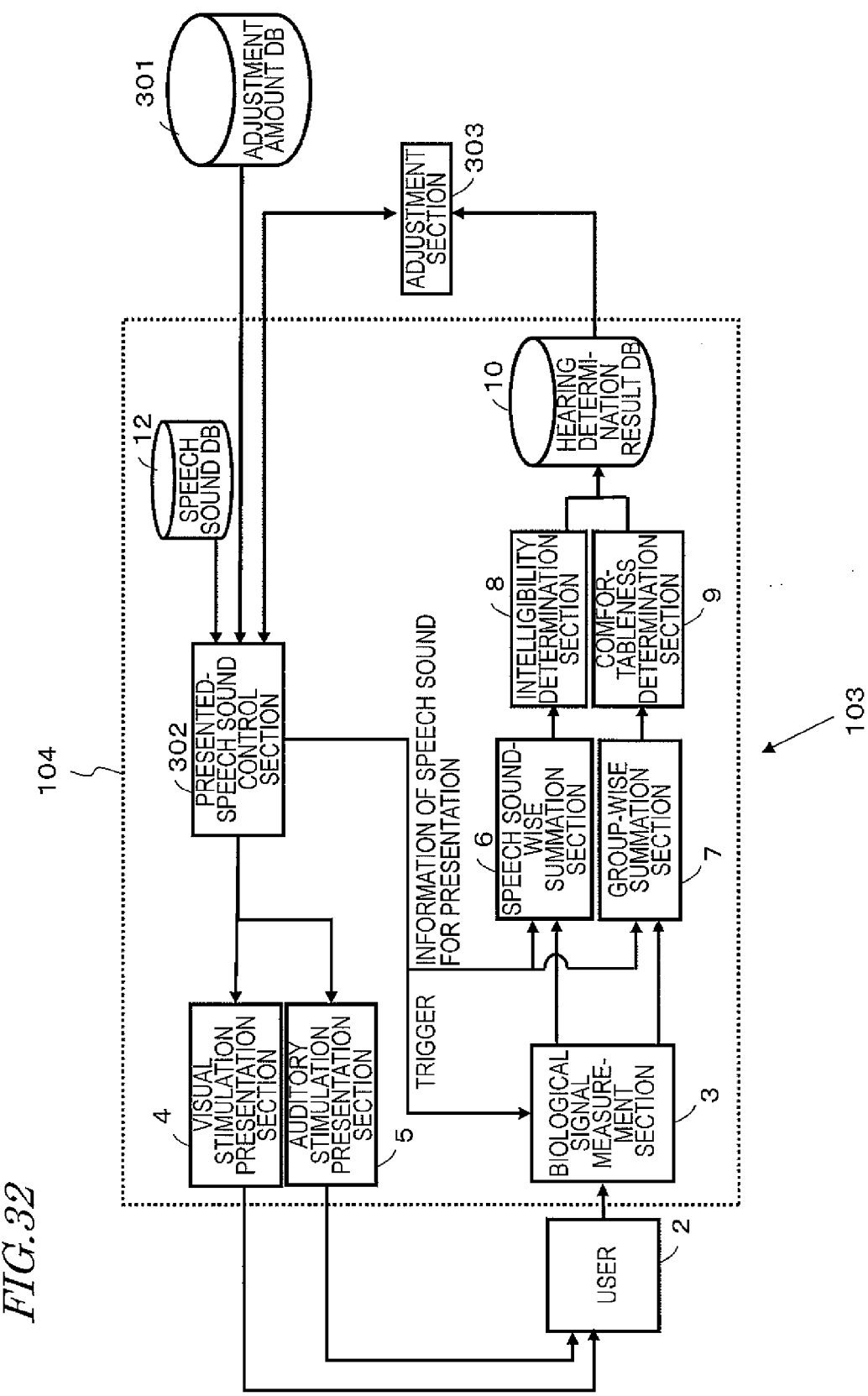
FIG. 32 is a diagram showing the construction of a hearing aid adjustment system 103 according to Embodiment 3.

FIG. 32 shows the construction of a hearing aid adjustment system 103 according to Embodiment 3. The hearing aid adjustment system 103 includes a hearing determination system 104, an adjustment amount DB 301, and an adjustment section 303. The component elements included in the hearing aid adjustment system 103 are interconnected in a wired or wireless manner so as to perform exchanges of information. Furthermore, the adjustment section 303 exchanges information with a hearing aid not shown, in a wired or wireless manner.

The hearing determination system 104 included in the hearing aid adjustment system 103 is identical in construction to that of Embodiment 1. The presented-speech sound control section 302 included in the hearing determination system 104 adjusts each determined speech sound by referring to the adjustment amount DB 301, unlike the presented-speech sound control section 11.

The adjustment amount DB 301 stores a plurality of values concerning adjustment amounts for a hearing aid. For example, FIG. 33 shows exemplary data stored in the adjustment amount DB 301. The adjustment amounts shown in FIG. 33 are indicative of sound pressure values which are incremented by 5 dB each. The adjustment amount DB 301 may contain amounts of amplification which are incremented by a value smaller than 5 dB. The adjustment amount DB 301 preferably contains values indicating amounts of amplification to be used for adjusting a hearing aid. Moreover, the adjustment amount DB 301 may values concerning acoustic aiding processes, e.g., directivity level, consonant emphasis, and noise reduction, or more specifically, information with which to adjust acoustic aiding processes. For example, FIG. 34 shows exemplary information with which to adjust acoustic aiding processes, the information being stored in the adjustment amount DB 301. In the case where acoustic aiding processes are introduced as additional functions concerning audio processes, as shown in FIG. 34, information indicating ON/OFF of the respective functions of directivity level, consonant emphasis, noise reduction may be contained. As used herein, (1) directivity level, (2) consonant emphasis, and (3) noise reduction pertain to the following functions.

(1) directivity level: The intelligibility does not change in itself. However, noises ascribable to impertinent sound sources are reduced, so that comfortableness is improved.

(2) consonant emphasis: Since the amount of gain adjustment in the consonant frequency band is increased, intelligibility is improved. However, comfortableness is deteriorated because the frequency characteristics of the audio itself are affected.

(3) noise reduction: Intelligibility is lowered because not only noise but also audio information is subjected to reduction. However, annoyance is decreased.

Although FIG. 34 show text characters of "ON" and "OFF", this is an example. The adjustment amount DB 301 may retain numerical values corresponding to "ON" and "OFF". For example, the adjustment amount DB 301 may retain a numerical value "1" corresponding to "ON", and a numerical value "0" corresponding to "OFF".

Referring to the speech sound DB 12, the presented-speech sound control section 302 determines a speech sound to be presented to the user 2. Unlike the presented-speech sound control section 11, the presented-speech sound control section 302 adjusts the determined speech sound. Specifically, the presented-speech sound control section 302 adjusts the determined speech sound by referring to the adjustment amount DB 301. Moreover, the presented-speech sound control section 302 sends information concerning the adjusted speech sound to the auditory stimulation presentation section 5. The auditory stimulation presentation section 5 presents the speech sound adjusted by the presented-speech sound control section 302 to the user 2.

The adjustment section 303 receives information of the presented speech sound from the presented-speech sound control section 302. The information of the speech sound includes the determined speech sound and an adjustment amount. Based on the result stored in the hearing measurement result DB 10, the adjustment section 303 determines whether the adjustment amount is appropriate or not. If it is not determined as an appropriate adjustment amount, the adjustment section 303 instructs the presented-speech sound control section 302 to make an adjustment with a different adjustment amount by referring to the adjustment amount DB 301.

If a determination result indicative of high annoyance has been obtained, the presented-speech sound control section 302 may make an adjustment with a smaller amount of amplification than the previous amount of amplification, for example.

FIG. 35 is a flowchart showing an overall processing procedure which is performed in the hearing aid adjustment system 103 of FIG. 32. The flowchart shown in FIG. 35 includes steps S31 and S32, unlike the flowchart of the hearing determination system 100 of Embodiment 1 (FIG. 24). The description of Embodiment 1 is relied on for any common component elements and process operations.

At step S31, referring to the results stored at step S20, the adjustment section 303 determines comfortableness and intelligibility. If comfortableness and intelligibility are determined to be within predetermined ranges, the adjustment section 303 determines that the presented-speech sound control section 302 is appropriately adjusted, and the process is ended. At this time, the adjustment section 303 may adjust the hearing aid based on the adjustment amount that has been determined as appropriate, or send information of the adjustment amount which has been determined as appropriate to the hearing aid.

On the other hand, if the adjustment section 303 determines that at least either one of comfortableness and intelligibility falls outside the predetermined range, the process proceeds to step S32. The adjustment section 303 outputs an instruction for changing the adjustment amount to the presented-speech sound control section 302. At step S32, based on the instruction received from the adjustment section 303, the presented-speech sound control section 302 reads information of a different adjustment amount by referring to the adjustment amount DB 301, and changes the adjustment amount.

At step S32 above, if a determination result indicative of a high annoyance has been obtained, the presented-speech sound control section 302 may read from the adjustment amount DB 301 information indicating an amount of amplification which is smaller than the previous amount of amplification, or turn noise reduction "ON", for example. If a determination result indicative of a high strife has been obtained, the presented-speech sound control section 302 may read from the adjustment amount DB 301 information indicating an amount of amplification which is greater than the previous amount of amplification, or turn directivity level processing "ON", for example. If a determination result indicative of a low intelligibility has been obtained, the presented-speech sound control section 302 may read from the adjustment amount DB 301 information indicating an amount of amplification which is larger than the previous amount of amplification, or turn consonant emphasis processing "ON", for example.

Thereafter, the process returns to step SS11, and a measurement is again conducted.

With the construction and operation described above, it is possible to adjust a determined speech sound and again perform a measurement.

A hearing determination apparatus according to the present disclosure and a hearing determination system incorporating the hearing determination apparatus allow a hearing determination to be made in a short period of time, and thus are applicable in the hearing determination for any person, not only those users who cannot bear long hours of restraint, e.g., physically handicapped users.

While the present invention has been described with respect to preferred embodiments thereof, it will be apparent to those skilled in the art that the disclosure may be modified in numerous ways and may assume many embodiments other than those specifically described above. Accordingly, it is intended by the appended claims to cover all modifications of the disclosure that fall within the true spirit and scope of the invention.

What is claimed is:

1. A determination system comprising:
one or more memories storing a speech sound database retaining data of a plurality of speech sounds and data defining at least one group within the plurality of speech sounds; and
circuitry which in operation is configured to:
measure an electroencephalogram signal of a user;
determine speech sounds to be presented to the user, by referring to the speech sound database;
present the determined speech sounds to the user as an audio;
present the determined speech sounds to the user as a character;
present the determined speech sounds to the user as a character;
by referring to the speech sound database, take a summation of event-related potentials of the electroencephalogram signal for each group of presented speech sounds;
from the event-related potentials having been subjected to summation for each group, determine an arithmetic-meaned electroencephalogram waveform and analyze a peak component of the arithmetic-meaned electroencephalogram waveform to make a group-by-group determination of comfortableness as to whether the user is comfortably hearing the presented speech sounds, to at least determine whether the user is listening to the presented speech sounds with strife, or to determine whether the user is annoyed by the speech sounds;
from the arithmetic-meaned electroencephalogram waveform analyze a peak component of the arithmetic-meaned electroencephalogram waveform to make a speech sound-by-speech sound determination of intelligibility as to whether the user is clearly hearing the presented speech sounds; and
output an adjustment amount for amplifying speech sounds based on the comfortableness and intelligibility determinations.

2. The determination system of claim 1, wherein the circuitry is configured to make a group-by-group determination of comfortableness based on whether the arithmetic-meaned electroencephalogram waveform for each group has a predetermined positive component in a range from 600 ms to 900 ms based on a point in time at which the audio of the speech sound is presented as a starting point, and has a predetermined negative component in a range from 100 ms to 300 ms.

3. The determination system of claim 2, wherein, circuitry in operation further is configured to:
determine whether the arithmetic-meaned electroencephalogram waveform for each group has a predetermined positive component in a range from 600 ms to 900 ms based on the point in time at which the audio of the speech sound is presented as a starting point;
determine whether the user is comfortably hearing the speech sound based on whether the arithmetic-meaned electroencephalogram waveform for each group has a predetermined negative component in a range from 100 ms to 300 ms based on the point in time at which the audio of the speech sound is presented as a starting point;
make a group-by-group determination of comfortableness based on the positive component determination result and the negative component determination result.

4. The determination system of claim 2, wherein the circuitry is configured to make a speech sound-by-speech sound determination of intelligibility based on whether the arithmetic-meaned electroencephalogram waveform for each speech sound has a predetermined positive component in a range from 200 ms to 400 ms or a range from about 400 ms to 600 ms based on a point in time at which the character of the speech sound is presented as a starting point.

5. The determination system of claim 1, wherein the circuitry is configured to make a speech sound-by-speech sound determination of intelligibility based on whether the arithmetic-meaned electroencephalogram waveform for each speech sound has a predetermined positive component in a range from 200 ms to 400 ms or a range from about 400 ms to 600 ms based on a point in time at which the character of the speech sound is presented as a starting point.

6. The determination system of claim 1, wherein, in the speech sound database, each of the plurality of speech sounds is categorized into the at least one group based on a predetermined rule.

7. The determination system of claim 6, wherein the at least one group includes a vowel group, a voiced consonant group, and an unvoiced consonant group.

8. The determination system of claim 6, wherein, in the speech sound database, each of the plurality of speech sounds is categorized into the at least one group based on a magnitude of probability of confusion.

9. The determination system of claim 6, wherein, when the circuitry determines whether the user is listening to the speech sound with strife, the at least one group is defined based on a presentation frequency of the speech sound.

10. The determination system of claim 6, wherein, when the circuitry determines whether the user is annoyed by the speech sound, the at least one group is defined in the speech sound database based on a type of the speech sound.

11. The determination system of claim 6, wherein,
the circuitry is configured to determine a number of presentations by which the speech sound is to be presented to the user;
in the speech sound database, each of the plurality of speech sounds is categorized into the at least one group based on a number of speech sounds; and
in accordance with the number of speech sounds of the at least one group, the circuitry is configured to determine a number of presentations by which the audio is to be presented and a number of presentations by which the character is to be presented.

12. The determination system of claim 1, wherein the circuitry is configured to determine a number of presentations by which the speech sound is to be presented to the user; and
the circuitry is configured continue to present the audio and character of the speech sound until the number of presentations for the audio and the number of presentations for the character are reached.

13. The determination system of claim 1, wherein,
the circuitry is configured to determine a number of presentations by which the speech sound is to be presented to the user; and
the circuitry is configured to determine that a specific speech sound is to be presented to the user a plurality of times.

14. The determination system of claim 13, wherein the circuitry is configured to determine the number of presentations based on an amplitude of the electroencephalogram signal of the user.

15. The determination system of claim 1, wherein the one or more memories further stores a hearing determination result database configured to store determination results output from the circuitry.

16. A determination system comprising:
circuitry which in operation is configured to:
determine speech sounds to be presented to a user by referring to a speech sound database retaining data of a plurality of speech sounds and data defining at least one group within the plurality of speech sounds, and to control additional circuitry configured to present the speech sounds as determined, to the user as an audio to present the speech sounds as determined, to the use as a character;
by referring to the speech sound database, take a summer of event-related potentials of an electroencephalogram signal of the user measured by a biological signal measurement device for each frequency of presented speech sounds;
from the event-related potentials having been subjected to summation for each frequency, determine an arithmetic-meaned electroencephalogram waveform and analyze a peak component of the arithmetic-meaned electroencephalogram waveform to make a frequency-by-frequency determination of comfortableness as to whether the user is comfortably hearing the presented speech sounds and to output a determination result; and
output an adjustment amount for amplifying speech sounds based on the comfortableness and intelligibility determinations.

17. A hearing aid adjustment system comprising:
circuitry which in operation is configured to:
measure an electroencephalogram signal of a user;
determine speech sounds to be presented to the user by referring to a speech sound database retaining data of a plurality of speech sounds and data defining at least one group within the plurality of speech sounds, and to adjust the determined speech sounds by referring to and adjustment amount database containing information for adjusting an amount of amplification for speech sounds or an acoustic aiding process;
present the adjusted speech sounds to the user as an audio;
present the adjusted speech sounds to the user as a character;
by referring to the speech sound database, take a summation of event-related potentials of the electroencephalogram signal for each group of presented speech sounds;
from the event-related potentials having been subjected to summation for each group, determine an arithmetic-meaned electroencephalogram waveform and analyze a peak component of the arithmetic-meaned electroencephalogram waveform to make a group-by-group determination of comfortableness as to whether the user is comfortably hearing the adjusted speech sounds, to at least determine whether the user is listening to the adjusted speech sounds with strife, or whether the user is annoyed by the adjusted speech sounds;
from the arithmetic-meaned electroencephalogram waveform, analyze a peak component of the arithmetic-meaned electroencephalogram waveform to make a speech sound-by-speech sound determination of intelligibility as to whether the user is clearly hearing the adjusted speech sounds;
determine that the adjustment amount is appropriate if the circuitry determines that the user is not listening to the adjusted speech sounds with strife or that the user is not annoyed by the adjusted speech sounds and the circuitry determines that the user is clearly hearing the adjusted speech sounds;
wherein the adjustment amount is based on the comfortableness and intelligibility determinations.

18. A determination method, comprising operating circuitry to perform the steps of:
measuring an electroencephalogram signal of a user;
determining speech sounds to be presented to the user, by referring to a speech sound database retaining data of a plurality of speech sounds and data defining at least one group within the plurality of speech sounds;
presenting the determined speech sounds determined by the step of determining to the user as an audio;
presenting the determined speech sounds determined by the step of determining to the user as a character;
by referring to the speech sound database, taking a summation of event-related potentials of the electroencephalogram signal for each group of presented speech sounds;
from the event-related potentials having been subjected to summation for each group, determining an arithmetic-meaned electroencephalogram waveform and analyzing a peak component of the arithmetic-meaned electroencephalogram waveform to make a group-by-group determination of comfortableness as to whether the user is comfortably hearing the presented speech sounds and outputting a determination result;
from the arithmetic-meaned electroencephalogram waveform, analyzing a peak component of the arithmetic-meaned electroencephalogram waveform to make a speech sound-by-speech sound determination of intelligibility as to whether the user is clearly hearing the presented speech sounds and outputting a determination result; and outputting an adjustment amount for amplifying speech sounds based on the comfortableness and intelligibility determinations.

19. A non-transitory computer-readable medium storing a computer program to be executed by a computer mounted in a hearing determination system, wherein the computer program causes the computer in the hearing determination system to execute the steps of:

receiving a measured electroencephalogram signal of a user;

determining speech sounds to be presented to the user, by referring to a speech sound database retaining data of a plurality of speech sounds and data defining at least one group within the plurality of speech sounds;

presenting the determined speech sounds determined by the step of determining to the user as an audio;

presenting the determined speech sounds determined by the step of determining to the user as a character;

by referring to the speech sound database, taking a summation of event-related potentials of the electroencephalogram signal for each group of presented speech sounds;

from the event-related potentials having been subjected to summation for each group, determining an arithmetic-meaned electroencephalogram waveform and analyzing a peak component of the arithmetic-meaned electroencephalogram waveform to make a group-by-group determination of comfortableness as to whether the user is comfortably hearing the presented speech sounds and outputting a determination result;

from the arithmetic-meaned electroencephalogram waveform, analyzing a peak component of the arithmetic-meaned electroencephalogram waveform to make a speech sound-by-speech sound determination of intelligibility as to whether the user is clearly hearing the presented speech sounds and outputting a determination result; and outputting an adjustment amount for amplifying speech sounds based on the comfortableness and intelligibility determinations.

* * * * *